(12) United States Patent
Schell et al.

(10) Patent No.: US 9,265,622 B2
(45) Date of Patent: Feb. 23, 2016

(54) PERCUTANEOUS ARTHRODESIS METHOD AND SYSTEM

(75) Inventors: Gerald Schell, Bay City, MI (US); Tracy Scott Anderson, Atlanta, GA (US); Alan Scott Davenport, Flowery Branch, GA (US); Kenneth Richard Barra, Acworth, GA (US)

(73) Assignee: Amendia, Inc., Marietta, GA (US)

( * ) Notice: Subject to any disclaimer, the term of this patent is extended or adjusted under 35 U.S.C. 154(b) by 865 days.

(21) Appl. No.: 13/028,310

(22) Filed: Feb. 16, 2011

(65) Prior Publication Data

US 2011/0230965 A1 Sep. 22, 2011

Related U.S. Application Data

(60) Provisional application No. 61/316,069, filed on Mar. 22, 2010.

(51) Int. Cl.
*A61F 2/44* (2006.01)
*A61B 17/17* (2006.01)
*A61B 17/70* (2006.01)
*A61F 2/46* (2006.01)
*A61B 17/16* (2006.01)
*A61F 2/28* (2006.01)
*A61F 2/30* (2006.01)

(52) U.S. Cl.
CPC ............ *A61F 2/447* (2013.01); *A61B 17/1757* (2013.01); *A61B 17/7064* (2013.01); *A61F 2/4455* (2013.01); *A61F 2/4611* (2013.01); *A61B 17/1671* (2013.01); *A61F 2002/2835* (2013.01); *A61F 2002/3008* (2013.01); *A61F 2002/30616* (2013.01); *A61F 2002/30904* (2013.01); *A61F 2002/4475* (2013.01); *A61F 2002/4627* (2013.01); *A61F 2002/4629* (2013.01); *A61F 2002/4677* (2013.01); *A61F 2250/0098* (2013.01)

(58) Field of Classification Search
USPC .............. 623/17.11–17.16; 606/99–100, 104, 606/86 A
See application file for complete search history.

(56) References Cited

U.S. PATENT DOCUMENTS

| | | | |
|---|---|---|---|
| 6,371,988 B1 * | 4/2002 | Pafford et al. ............. | 623/17.11 |
| 7,311,734 B2 * | 12/2007 | Van Hoeck ............. | A61F 2/442 606/99 |
| 2004/0127990 A1 * | 7/2004 | Bartish et al. ............. | 623/17.11 |
| 2006/0276902 A1 * | 12/2006 | Zipnick ............. | A61B 17/1671 623/17.16 |
| 2006/0293748 A1 * | 12/2006 | Alexander et al. ......... | 623/17.11 |

(Continued)

OTHER PUBLICATIONS

NonFinal Rejection issued Feb. 17, 2012, in U.S. Appl. No. 13/294,544.

(Continued)

*Primary Examiner* — Anu Ramana
*Assistant Examiner* — Jessica Weiss
(74) *Attorney, Agent, or Firm* — David L. King

(57) ABSTRACT

A method and system for percutaneous fusion to correct disc compression is presented. The method has several steps, for instance, inserting a percutaneous lumbar interbody implant; positioning guide wires for each facet screw to be implanted; performing facet arthrodesis in preparation for the facet screws; fixating the plurality of facet screws; and optionally performing foramen nerve root or central decompression. The system includes an implant, an elongate cannulated insertion tool, and an elongate lockshaft positioned within the insertion tool.

13 Claims, 29 Drawing Sheets

(56) References Cited

U.S. PATENT DOCUMENTS

| | | | | |
|---|---|---|---|---|
| 2007/0162046 | A1* | 7/2007 | Vandewalle | A61B 17/8875 606/108 |
| 2007/0173954 | A1* | 7/2007 | Lavi | A61B 17/562 623/21.11 |
| 2008/0262623 | A1* | 10/2008 | Bagga et al. | 623/17.16 |
| 2009/0138015 | A1* | 5/2009 | Conner et al. | 606/80 |
| 2011/0112587 | A1* | 5/2011 | Patel et al. | 606/86 A |

OTHER PUBLICATIONS

Response to NonFinal Rejection submitted May 17, 2012 in U.S. Appl. No. 13/294,544.

* cited by examiner

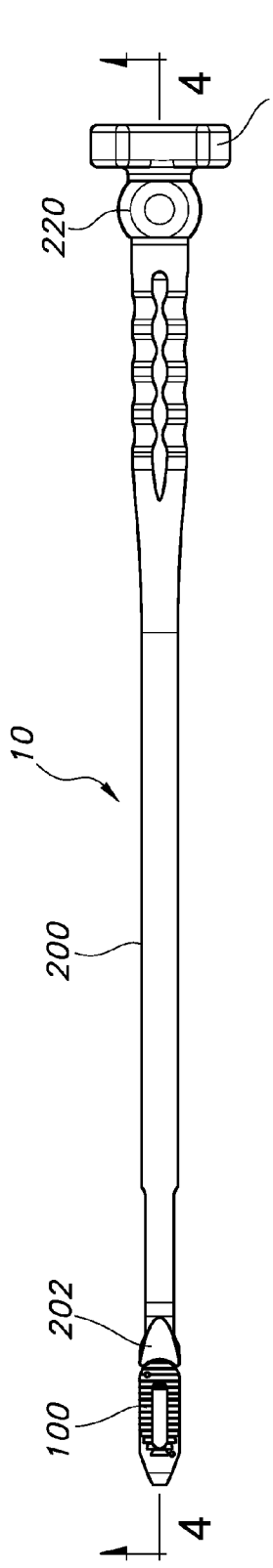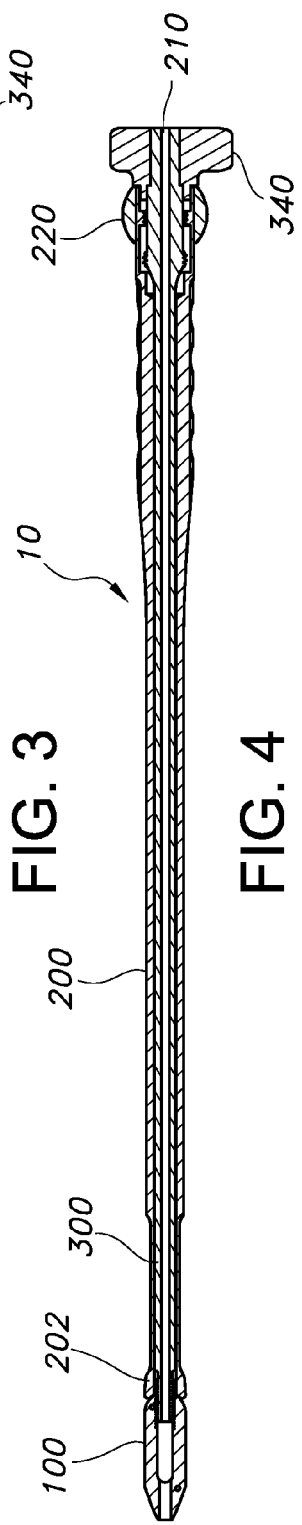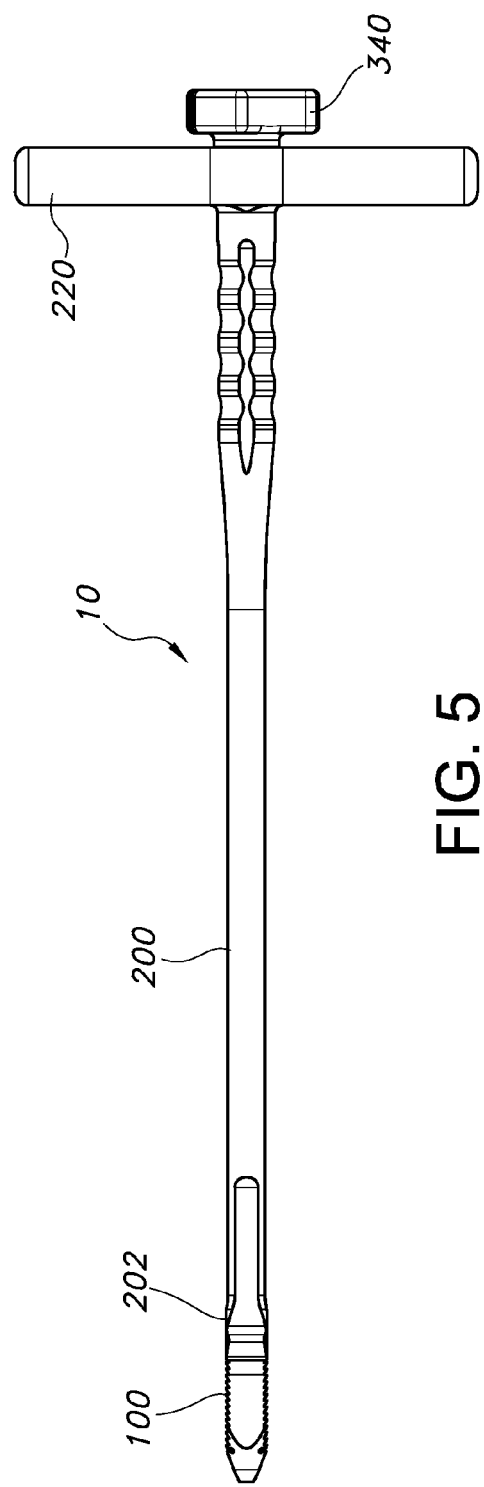

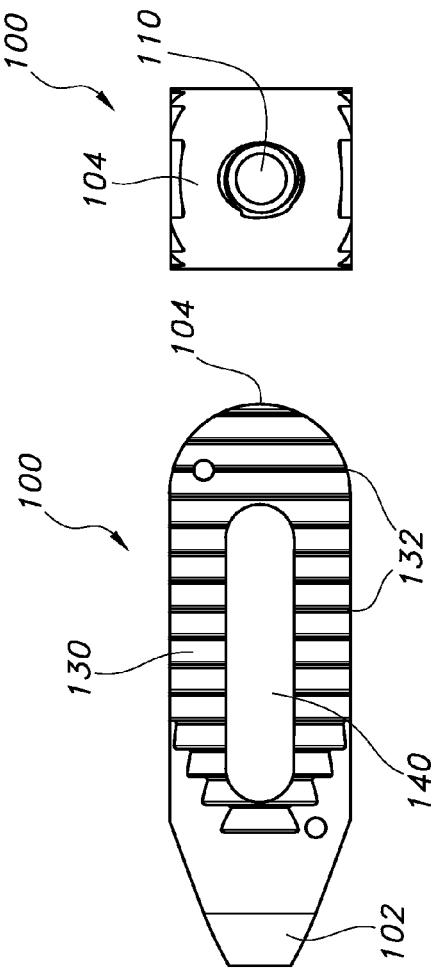
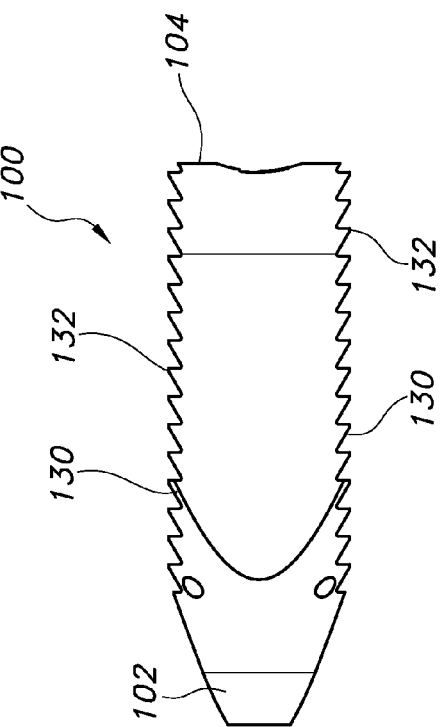
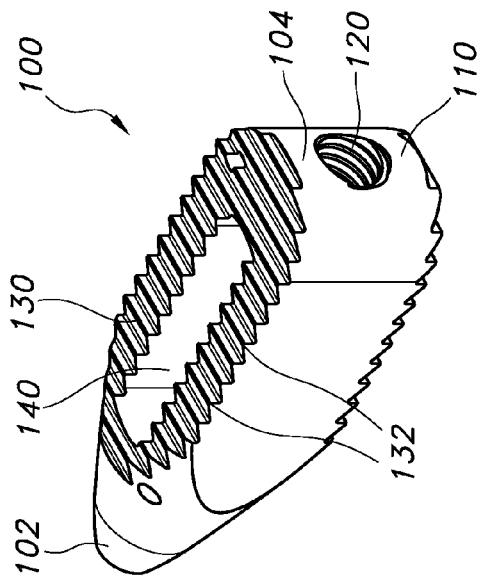
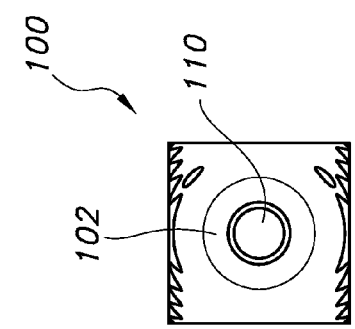

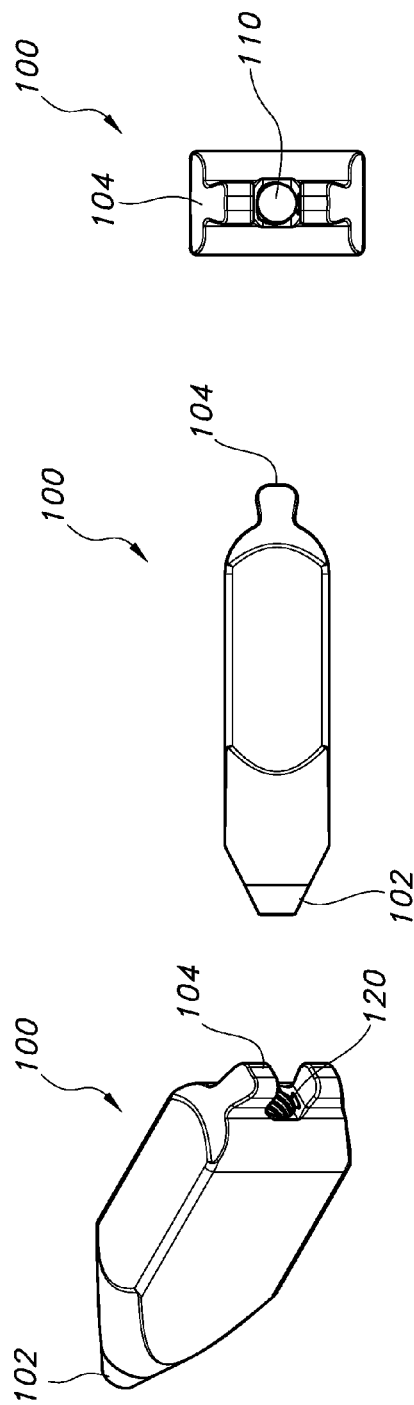
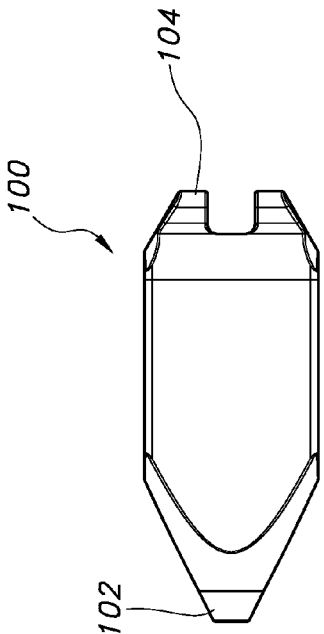
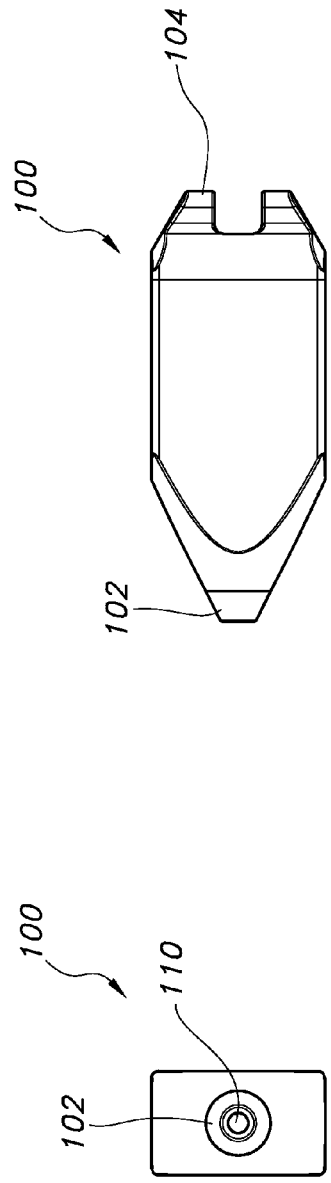
FIG. 11
FIG. 12
FIG. 13
FIG. 14
FIG. 15

PERCUTANEOUS ARTHRODESIS METHOD AND SYSTEM

CONTINUITY

This application claims the benefit of and priority to U.S. Provisional Application 61/316,069, titled PERCUTANEOUS ARTHRODESIS METHOD, which was filed on Mar. 22, 2010.

FIELD OF THE INVENTION

Presented herein is a percutaneous arthrodesis method and system. More specifically, a method and system for minimally invasive 3-point fusion is presented.

BACKGROUND OF THE INVENTION

There are several procedures available to patients with degenerative spine conditions. For example, Anterior Lumbar Interbody Fusion ("ALIF") has been performed by surgeons since the 1950's. In an ALIF procedure, the disc space is fused by approaching the spine through the abdomen. In the ALIF approach, a three-inch to five-inch incision is made on the left side of the abdomen and the abdominal muscles are retracted to the side. Since the anterior abdominal muscle in the midline (rectus abdominis) runs vertically, it does not need to be cut and easily retracts to the side. The abdominal contents lay inside a large sack (peritoneum) that can also be retracted, thus allowing the spine surgeon access to the front of the spine without actually entering the abdomen. There is also a less popular transperitoneal approach that accesses the spine through the abdomen. This adds a lot of unnecessary morbidity to the procedure and therefore is used much less often.

Another technique is called Posterior Lumbar Interbody Fusion ("PLIF"). In the PLIF approach, the spine is accessed through a three-inch to six-inch long incision in the midline of the back and the left and right lower back muscles are stripped off the lamina and spinous process on both sides and at multiple levels. After the spine is approached, the lamina and spinous process is removed, which allows visualization of the nerve roots. The facet joints, which are directly over the nerve roots, may then be undercut to give the nerve roots more room. The nerve roots are then retracted to one side and the disc space is cleaned of the disc material. A bone graft, or an interbody cage, is then inserted into the disc space and the bone grows from vertebral body to vertebral body.

Still another procedure is a Transforaminal Lumbar Interbody Fusion ("TLIF"). By removing the entire facet joint, visualization into the disc space is improved and more disc material can be removed. It should also provide for less nerve retraction. Because one entire facet is removed, it is only done on one side. Removing the facet joints on both sides of the spine would result in too much instability. With increased visualization and room for dissection, a larger implant and/or bone graft can be used. Although this has some improvements over a PLIF procedure, the anterior approach, in most cases still provides the best visualization, most surface area for healing, and the best reduction of any of the approaches to the disc space.

There are other approaches know in the art, as well. For instance, Direct Lateral Interbody Fusion, Axial Lumbar Interbody Fusion using a transsacral approach, and the like. Those skilled in the art will appreciate that these and other known procedures have benefits, as well as disadvantages.

There are also many types of stabilization systems available. One type of spinal stabilization system includes screws and connecting rods which can be used for stabilizing many spinal conditions including, for example, degenerative disc disease, scoliosis, spondylolithisis and spinal stenosis. In these systems, a bone screw (e.g., pedicle screw) is typically anchored into each vertebral body to be stabilized and a rigid connecting rod mounted to the screws to fix the vertebrae in a particular relative position.

Another type of spinal stabilization system includes interbody implants. Some of these implants are bone, PEEK, solid titanium or similar non-bone implant material and some are hollow implants that provide for inclusion of a bone graft or other suitable material to facilitate bony union of the vertebrae.

Interbody implants can be inserted into the disc space through an anterior, posterior or lateral approach. In some systems, the implants are inserted into a bore formed between adjacent vertebral bodies in the cortical endplates and can extend into the cancellous bone deep to the cortical endplates. Implant size is typically selected such that the implants force the vertebrae apart to cause tensing of the vertebral annulus and other soft tissue structures surrounding the joint space. Tensing the soft tissues surrounding the joint space results in the vertebrae exerting compressive forces on the implant to maintain the implant in place.

Accordingly, there is a continuing need for improved vertebral stabilizing devices and methods. The system and apparatuses described herein are directed to addressing these needs.

SUMMARY

Presented herein are a system and method for percutaneous fusion to correct disc compression. In one aspect, the system comprises an implant defining at least one implant aperture, an elongate cannulated insertion tool defining an interior insertion tool pathway, and an elongate lockshaft positioned therein the insertion tool pathway and defining a longitudinal interior lockshaft pathway.

The method comprises several steps, which may or may not be performed in the particular order discussed. As one skilled in the art can appreciate, the methods herein are not meant to be limited and only serve as a description of the method in its best known manner.

The method, in one aspect, comprises making an incision to access a desired spinal motion segment, locating a path to the disc space at the desired target level, inserting a guide wire, inserting a spinal implant into the disc space at a desired position, removing the guide wire, and fixating a portion of the desired spinal motion segment.

BRIEF DESCRIPTION OF THE DRAWINGS

These and other features of the preferred embodiments of the present invention will become more apparent in the detailed description in which reference is made to the appended drawings wherein:

FIG. 3 is a side elevational view of the Lumbar Interbody Fusion system of FIG. 1;

FIG. 4 is a cut-away side elevational view Lumbar Interbody Fusion system of FIG. 1, cut along line 4-4 of FIG. 3;

FIG. 5 is a plan view of the Lumbar Interbody Fusion system of FIG. 1;

FIG. 6 is a perspective view of one aspect for an implant used in a Lumbar Interbody Fusion system;

FIG. 7 is a plan view of the implant of FIG. 6;

FIG. 8 is front elevational view of the implant of FIG. 6;

FIG. 9 is a rear elevational view of the implant of FIG. 6;

FIG. 10 is a side elevational view of the implant of FIG. 6;

FIG. 11 is a perspective view of one aspect for an implant used in a Lumbar Interbody Fusion system;

FIG. 12 is a plan view of the implant of FIG. 11;

FIG. 13 is front elevational view of the implant of FIG. 11;

FIG. 14 is a rear elevational view of the implant of FIG. 11;

FIG. 15 is a side elevational view of the implant of FIG. 11;

DETAILED DESCRIPTION OF THE INVENTION

Figure 1:
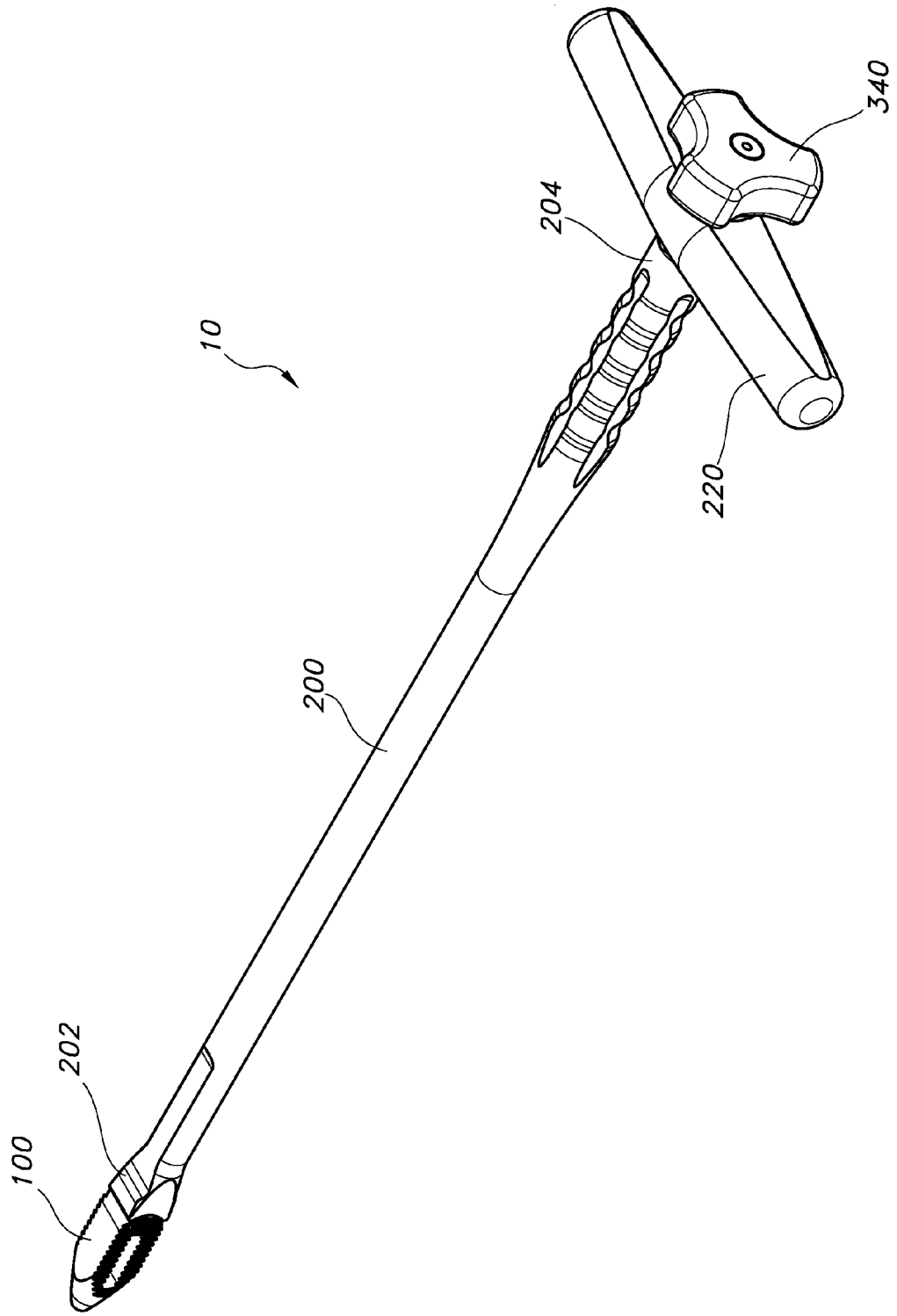
FIG. 1 is a perspective view of one aspect of an Lumbar Interbody Fusion system.

The present systems and apparatuses and methods are understood more readily by reference to the following detailed description, examples, drawing, and claims, and their previous and following description. However, before the present devices, systems, and/or methods are disclosed and described, it is to be understood that this invention is not limited to the specific devices, systems, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention in its best, currently known embodiment. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used throughout, the singular forms "a," "an" and "the" include plural referents unless the context clearly dictates otherwise. Thus, for example, reference to "a screw" can include two or more such screws unless the context indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

Presented herein is a percutaneous arthrodesis method and system 10 to correct disc compression. The system comprises an elongated spinal implant 100 having a square or rectangular profile defined by the overall height and width. The implant 100 that, in one aspect, defines at least one implant aperture 110. The implant 100 is sized for insertion between two adjacent vertebrae.

In another aspect, the system 10 also comprises an elongate cannulated insertion tool 200 defining an interior insertion tool pathway 210. The insertion tool 200 is configured to position the implant into the desired position between two spinal vertebrae. In an exemplified aspect, the distal end 202 of the elongate cannulated insertion tool matingly engages at least a portion of at least one external surface of the implant.

Figure 2:
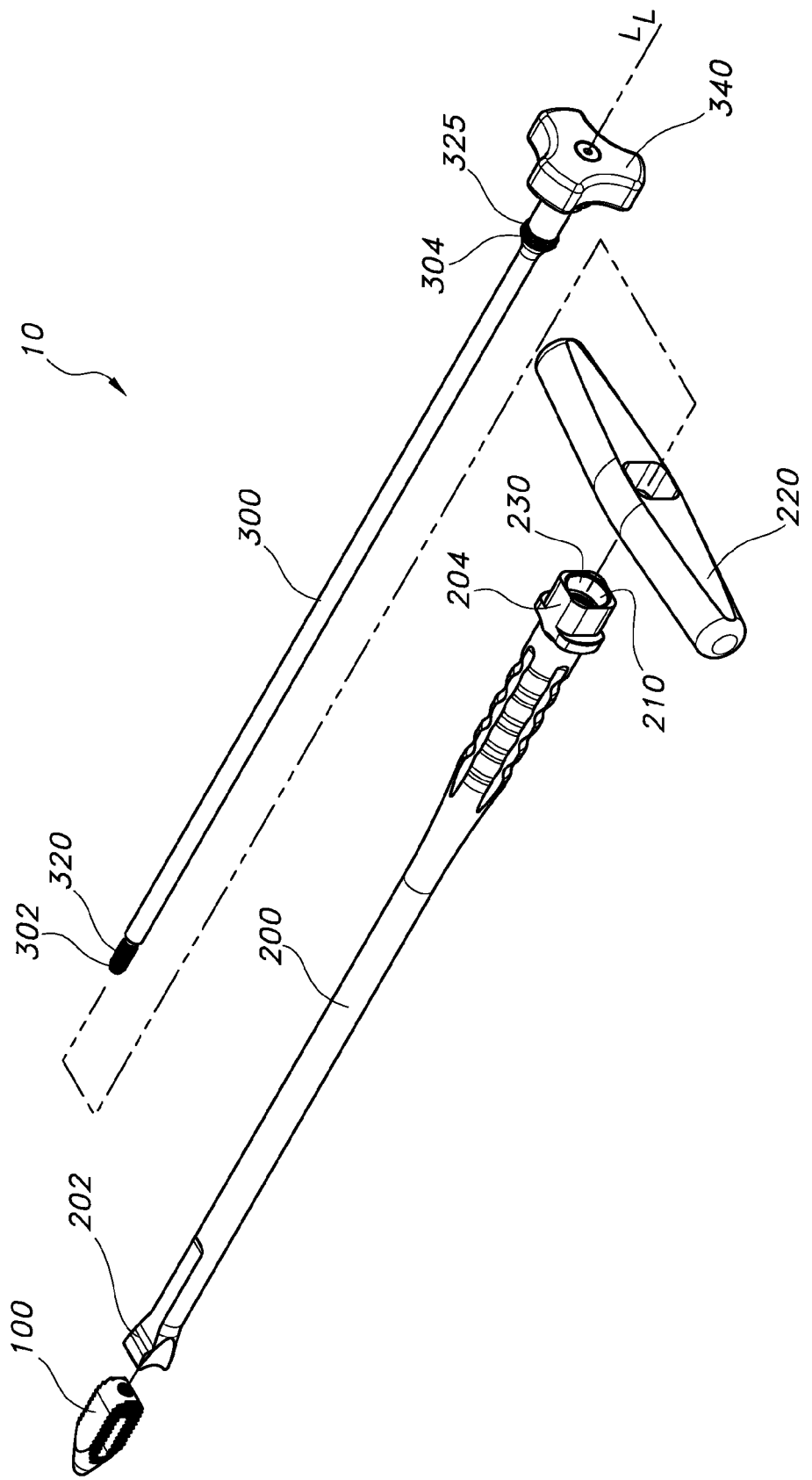
FIG. 2 is a partially exploded perspective view of the Lumbar Interbody Fusion system of FIG. 1.
Figure 16:
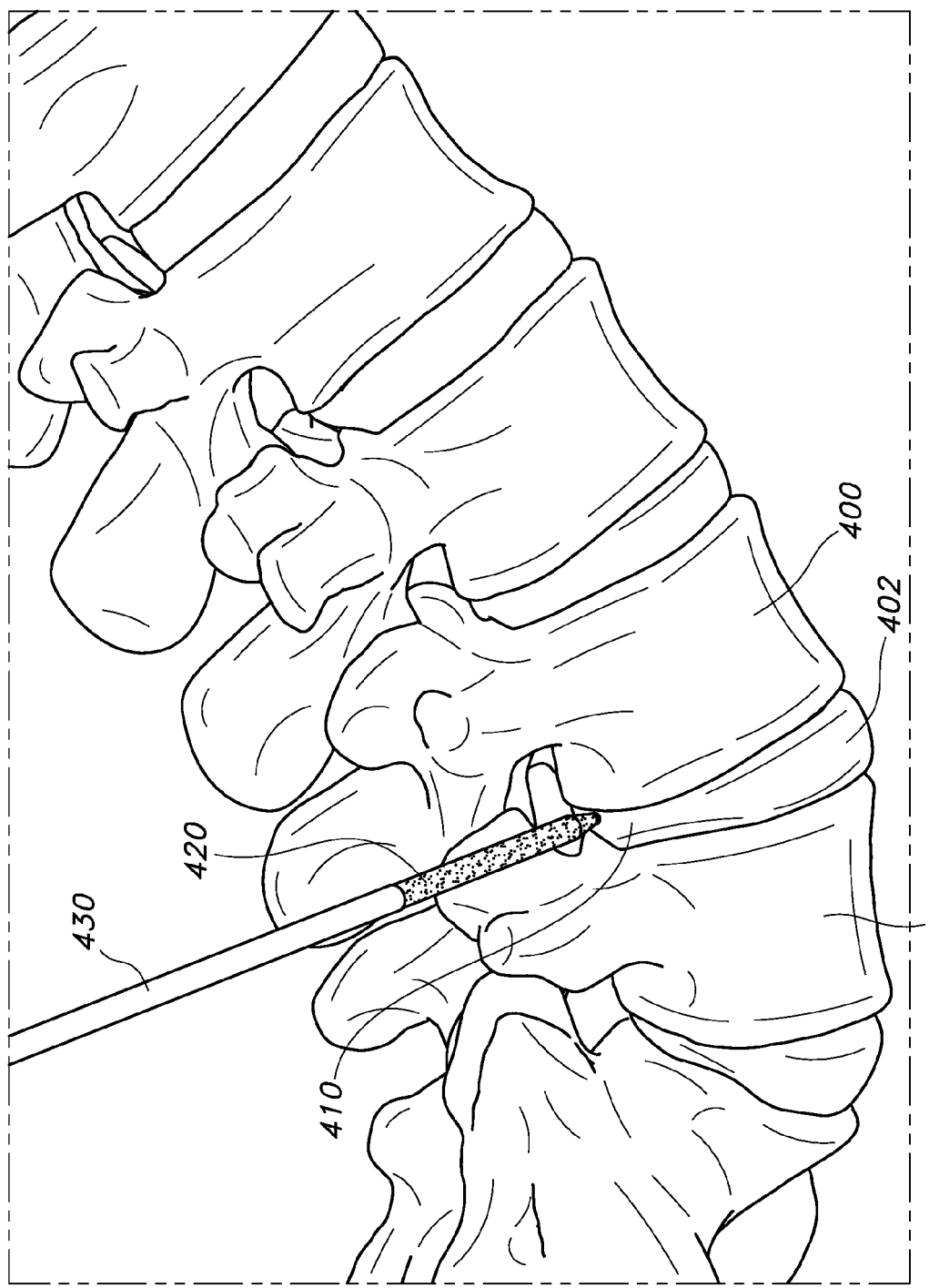
FIG. 16 is a perspective view of one aspect of a percutaneous arthrodesis method, showing the step of positioning a nerve monitoring probe with a transfer sleeve through Kambin's triangle.
Figure 17:
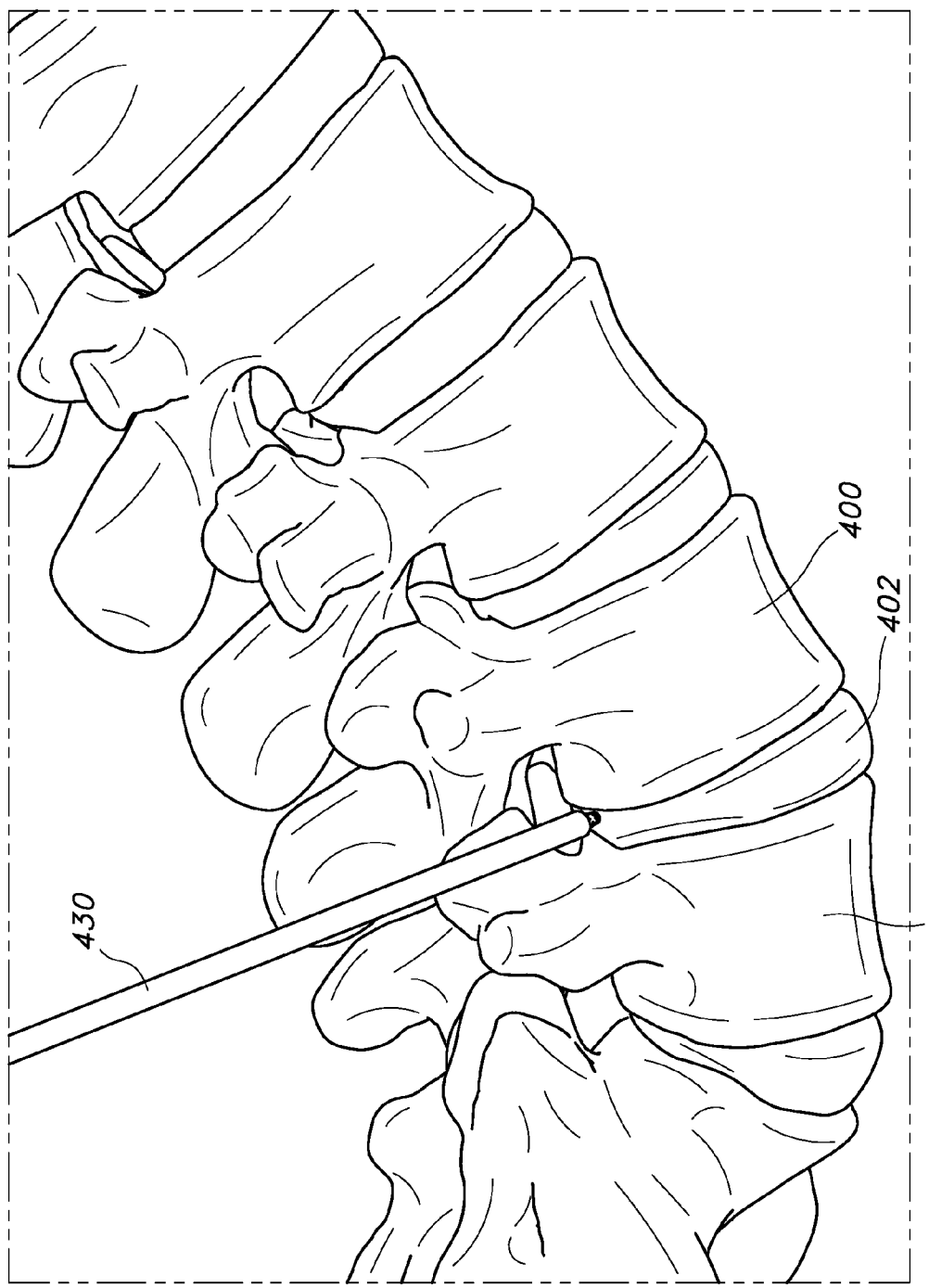
FIG. 17 is a perspective view of the method of FIG. 16, showing the step of advancing the transfer sleeve to contact a portion of the annulus for removal of the probe.
Figure 18:
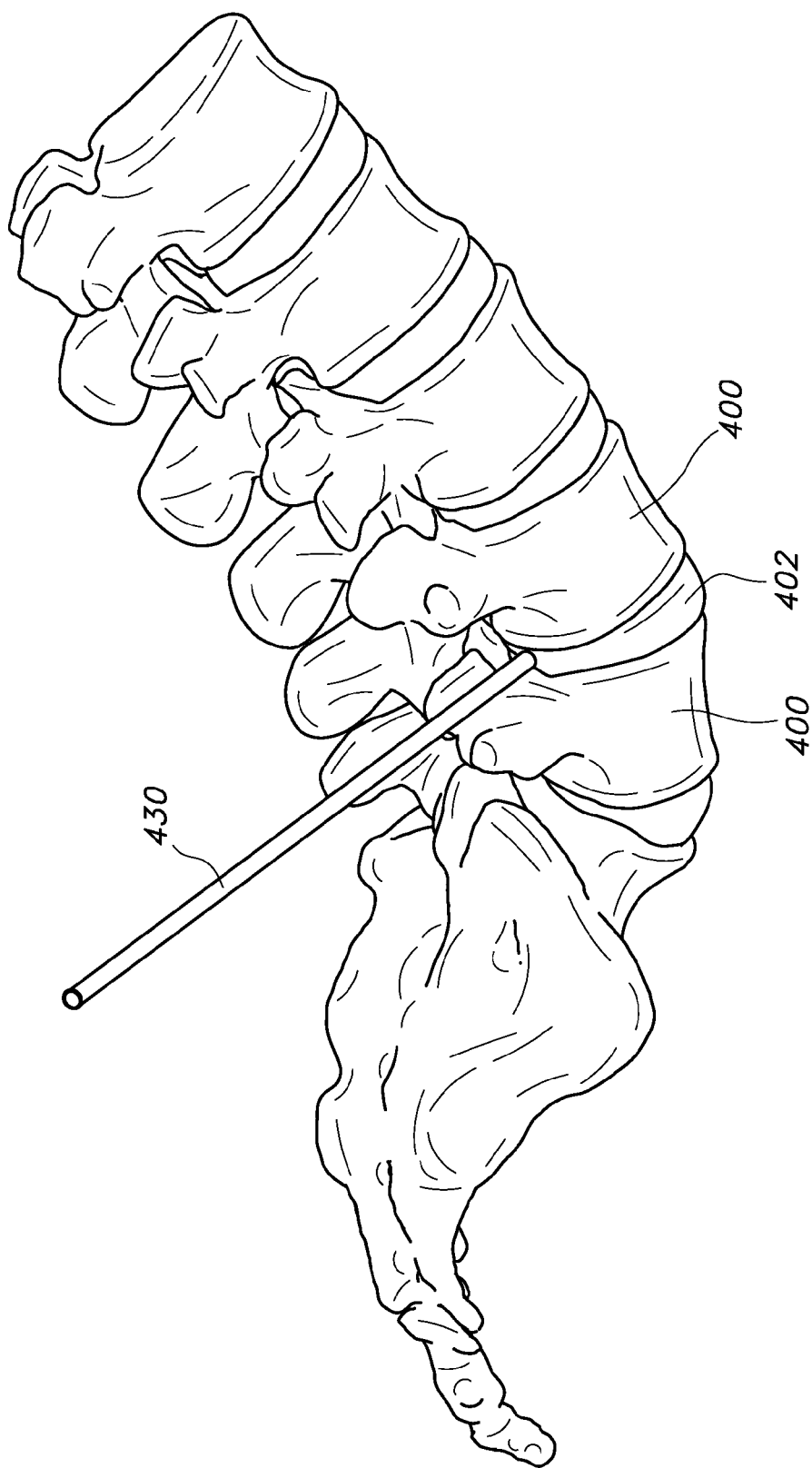
FIG. 18 is a perspective view of the method of FIG. 16, showing the step of removing the nerve monitoring probe, leaving the transfer sleeve in place.
Figure 19:
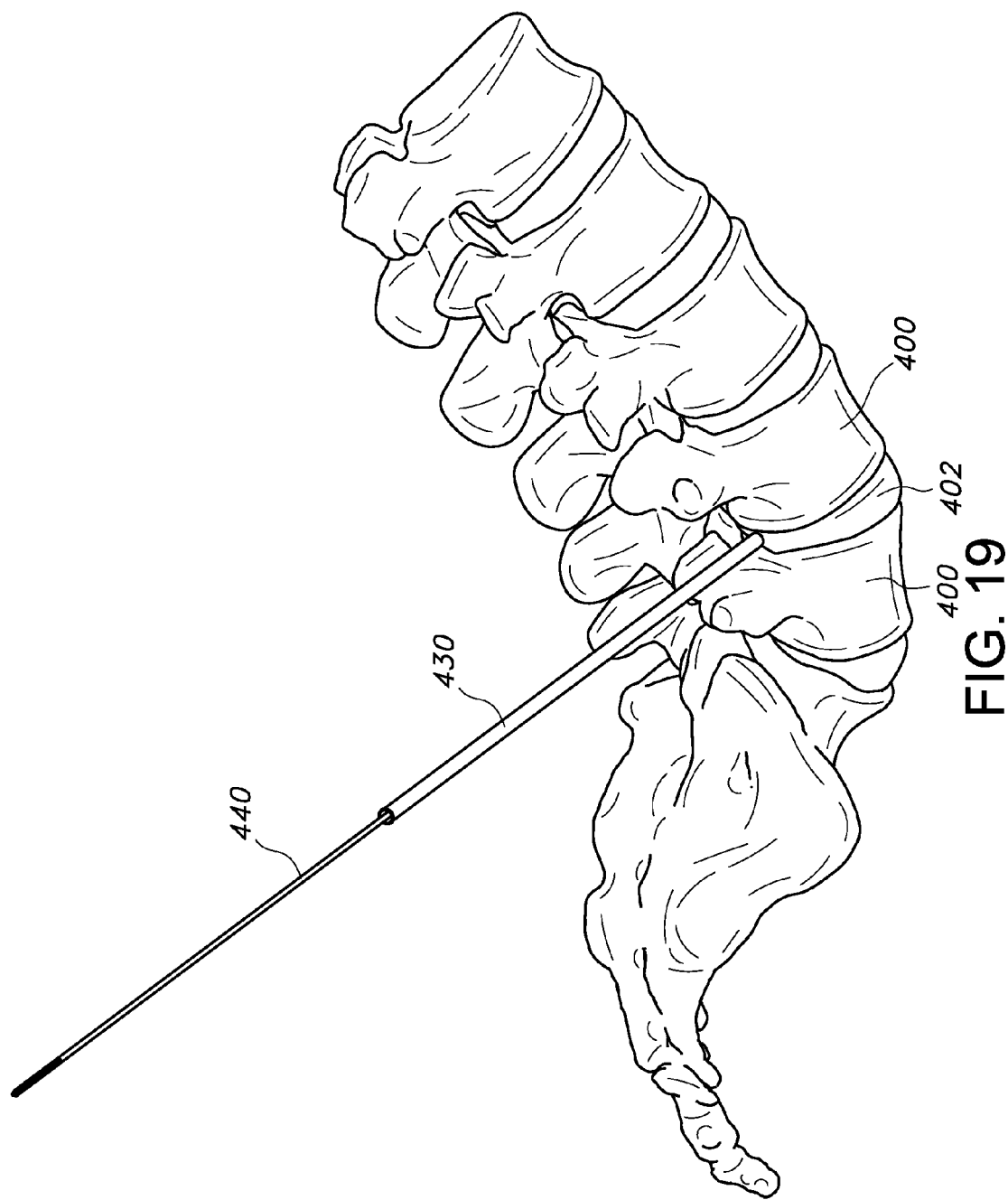
FIG. 19 is a perspective view of the method of FIG. 16, showing the step of inserting a guide wire through the transfer sleeve to maintain a path to the disc space.
Figure 20:
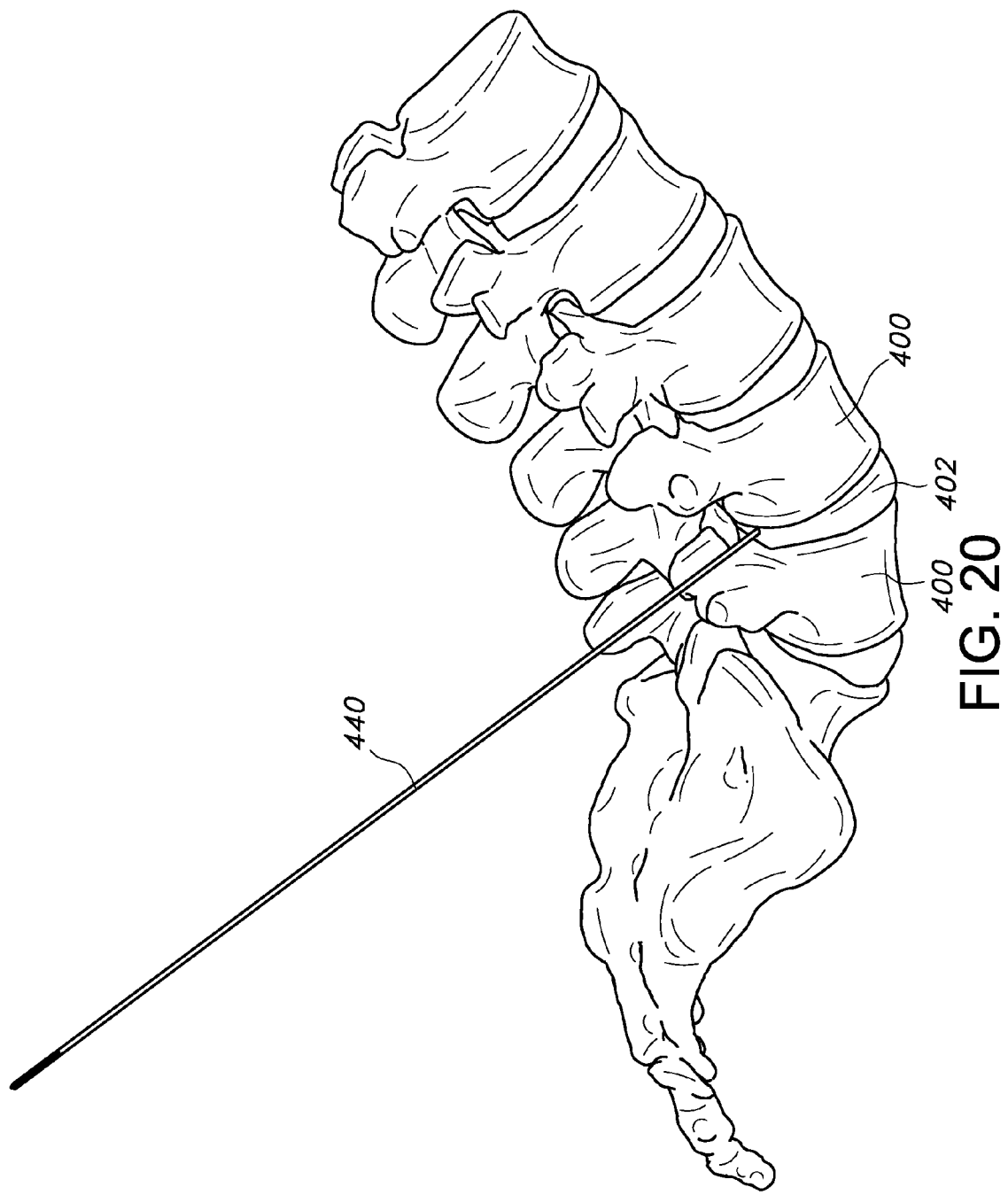
FIG. 20 is a perspective view of the method of FIG. 16, showing the step of removing the transfer sleeve and leaving the guide wire in place.
Figure 21:
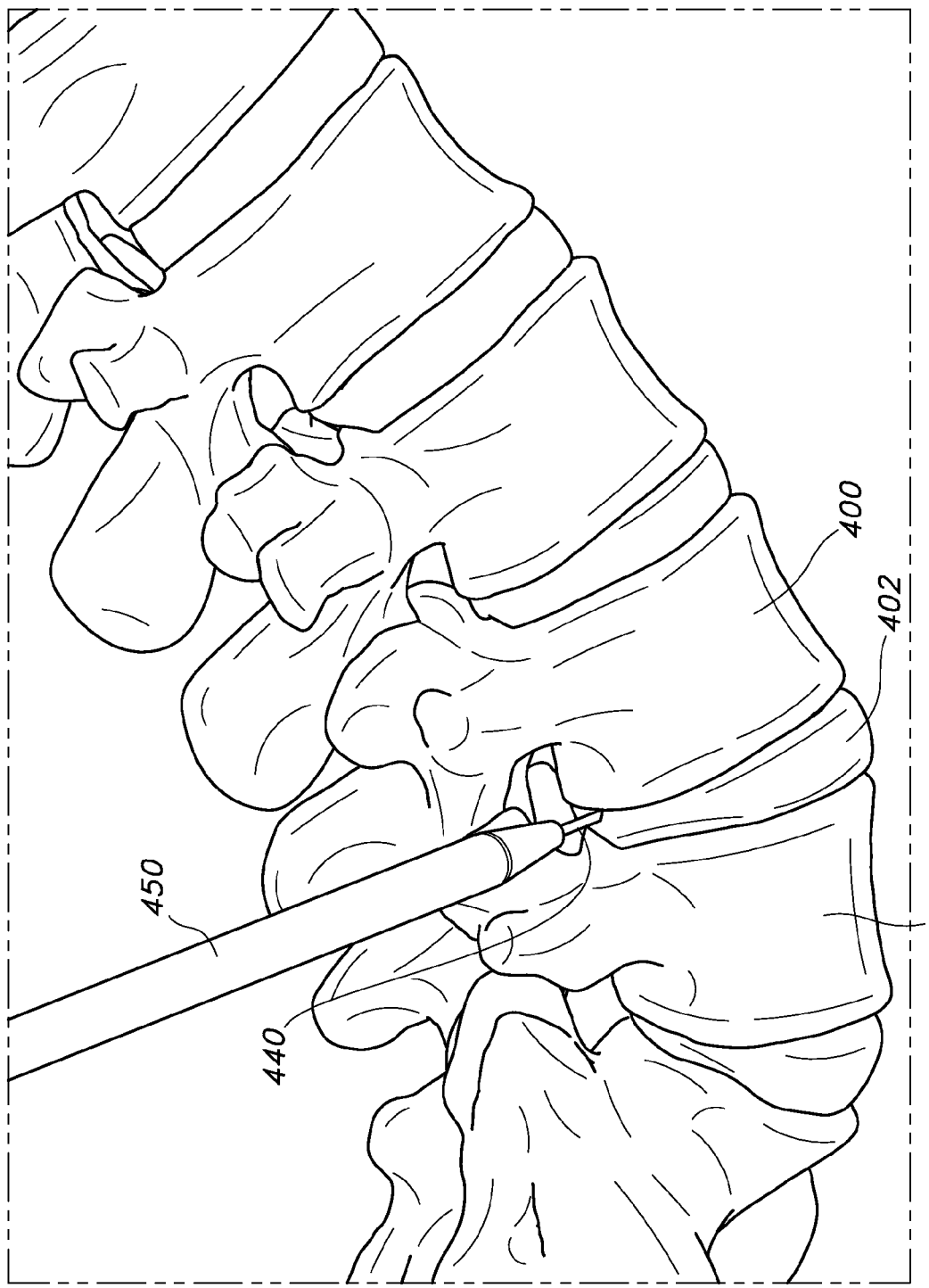
FIG. 21 is a perspective view of the method of FIG. 16, showing the step of advancing a dilator over the guide wire.
Figure 22:
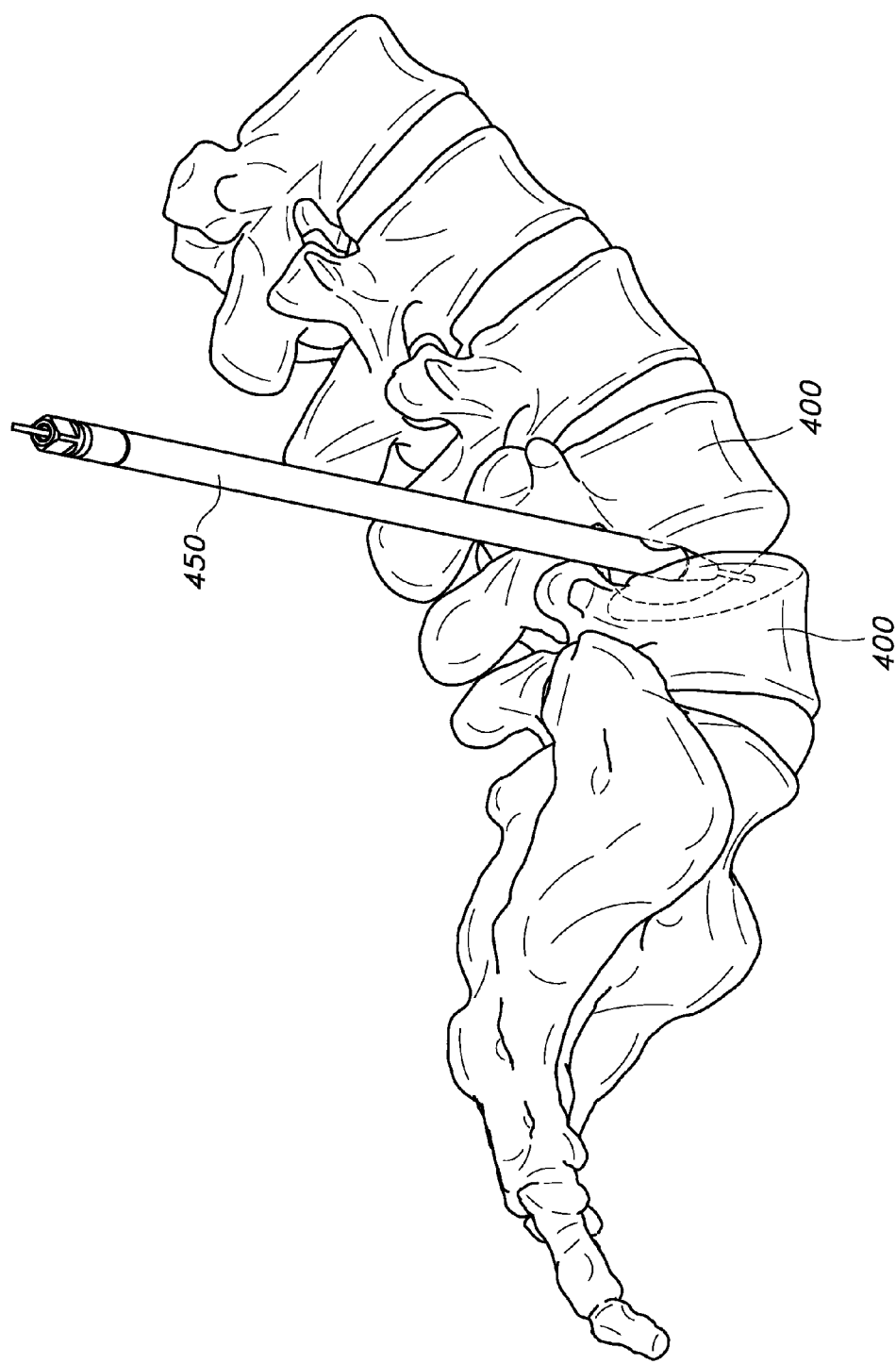
FIG. 22 is a partially transparent perspective view of the method of FIG. 16, showing the step of pushing a dilator into the disc space to distract the vertebral bodies.
Figure 23:
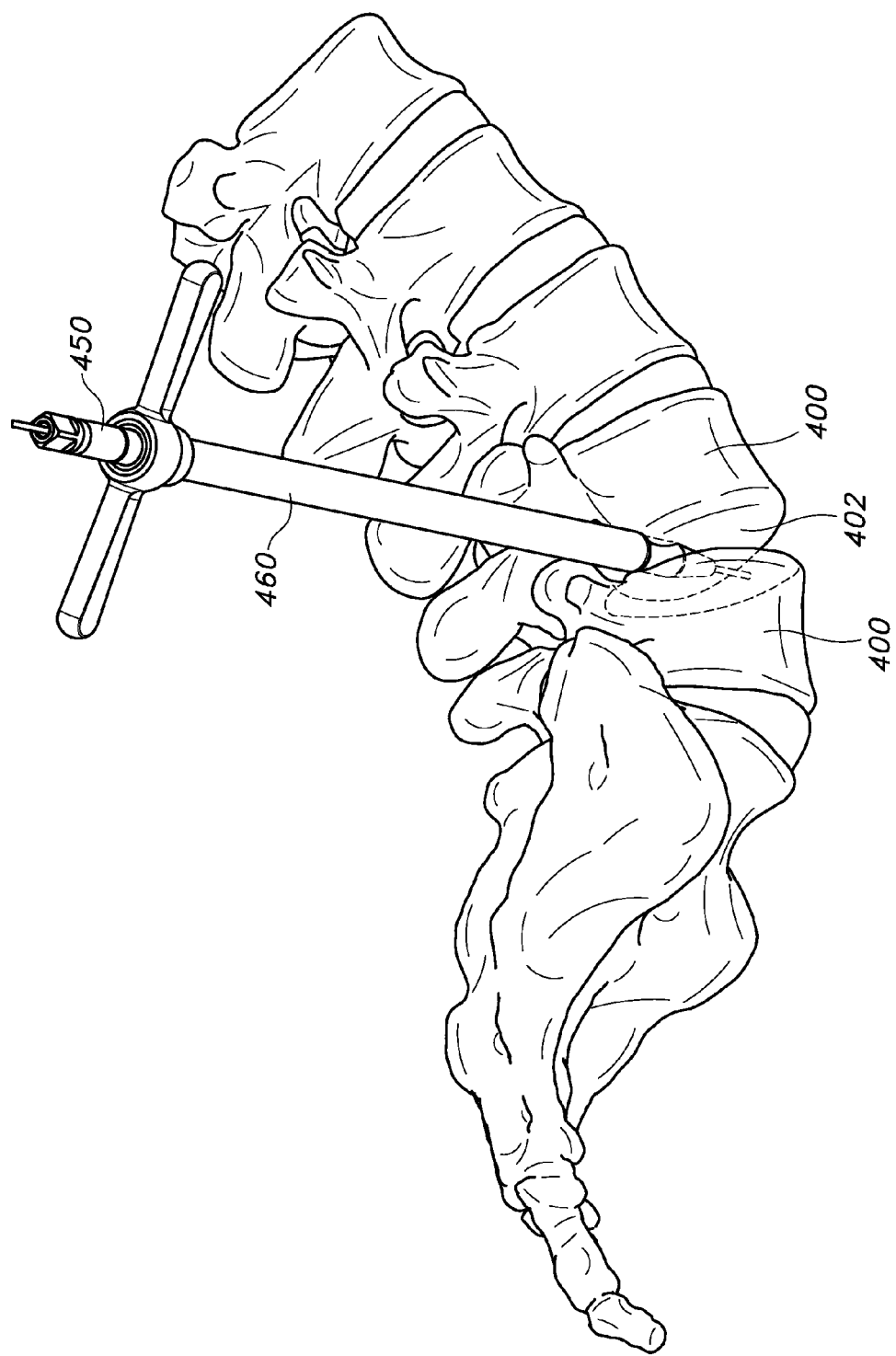
FIG. 23 is a partially transparent perspective view of the method of FIG. 16, showing the step of positioning an access portal into the disc space.
Figure 24:
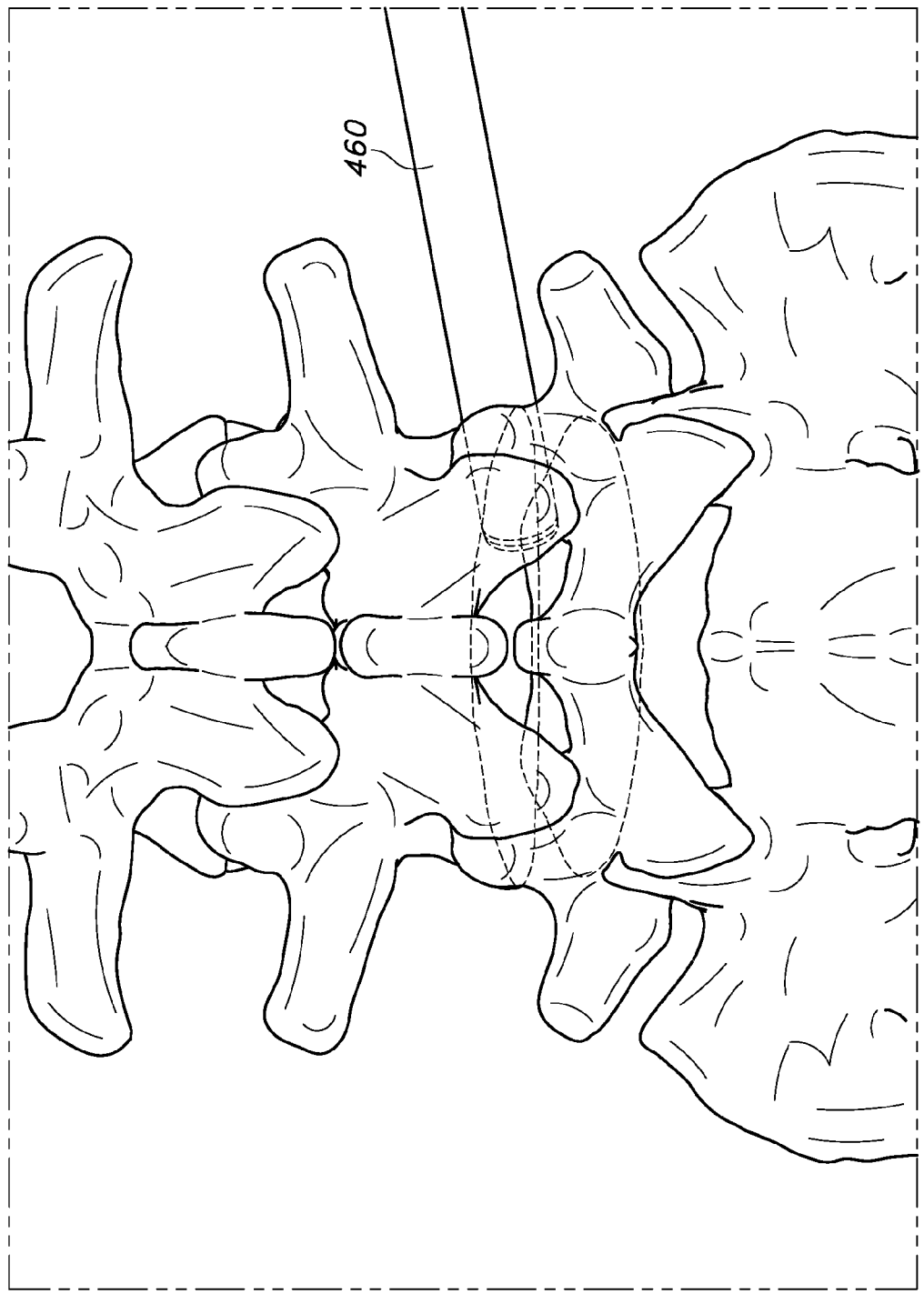
FIG. 24 is a partially transparent perspective view of the method of FIG. 16, showing the step of removing the dilator and the guide wire, leaving the access portal in place.
Figure 25:
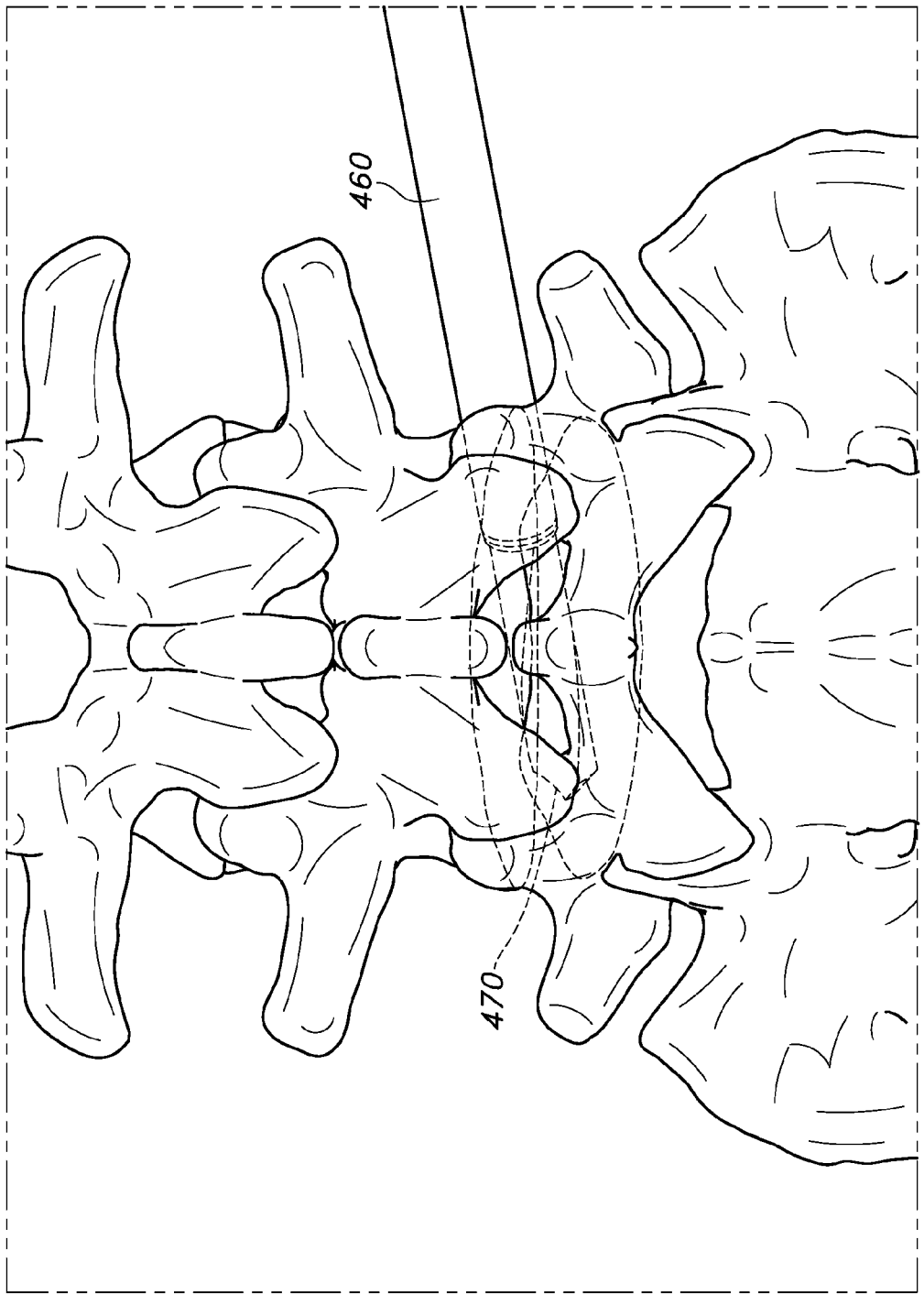
FIG. 25 is a partially transparent perspective view of the method of FIG. 16, showing the step of performing a discectomy and decorticating the vertebral endplates by first drilling to access the nucleus.

As illustrated in FIG. 2, the insertion tool 200, in one aspect, has an elongate lockshaft 300 positioned therein the insertion tool pathway 210 and defining a longitudinal interior lockshaft pathway 310, wherein a distal end 302 of the elongate lockshaft 300 selectively engages a portion of the implant. In an exemplified aspect, when the distal end 302 of the elongate lockshaft is engaged with the implant 100, the interior lockshaft pathway 310 and the implant aperture 110 are substantially coaxial. In this aspect, the implant aperture can extend therethrough the implant, but does not necessarily do so. In this aspect, however, the implant aperture and the interior lockshaft pathway are configured for the acceptance of a guide wire.

The lockshaft 300, for example, can be configured to engage the implant 100 in order to maintain rotational alignment of the implant with respect to the insertion tool. In this aspect, rotation of the elongate cannulated insertion tool would, in turn, rotate the implant along its longitudinal axis $I_L$. In one aspect, at least a proximal portion of the implant aperture comprises internal threads 120 and at least a portion of the distal end of the elongate lockshaft comprises external threads 320 that mate with the internal threads 120 of the implant aperture 110.

In one exemplified aspect, a handle 220 can be positioned in a proximal portion 204 of the elongate cannulated insertion tool 200. The handle 220 provides visual means to determine the rotational orientation of the implant 100. Of course, other visual means for determining orientation can also be employed. For example, and not meant to be limiting, the cannulated insertion tool can comprise markings or etchings along the length of the shaft. The handle also provides the practitioner with an easy means with which to turn the implant after insertion.

As mentioned above, the elongate lockshaft 300 can engage the implant for insertion and positioning. In some instances, it is beneficial for the elongate lockshaft to be configured to translate longitudinally within the elongate cannulated insertion tool. In this aspect, once the elongate lockshaft attaches to a portion of the implant, the implant can be drawn into tighter engagement with the elongate cannulated insertion tool. In one exemplified aspect, the proximal end 204 of the elongate cannulated insertion tool comprises internal threads 230 and at least a portion of a proximal end 304 of the elongate lockshaft 300 comprises external threads 325 that mate with the internal threads 230 of the cannulated insertion tool 200. As such, in this aspect, rotation of the lockshaft in a clockwise direction moves the lockshaft longitudinally within the cannulated insertion tool in a first direction and rotation of the lockshaft in a counterclockwise direction moves the lockshaft 300 longitudinally within the cannulated insertion tool in a second, opposed direction. In a further aspect, a knob 340 is positioned on a portion of the proximal end 304 of the lockshaft to enable the rotation of the lockshaft about its longitudinal axis $L_L$. Other methods of translating the lockshaft longitudinally within the cannulated inserted are also contemplated.

In addition to the threaded engagement of the lockshaft 300 and the implant 100, in one aspect, the distal end 202 of the elongate cannulated insertion tool is configured to mate with at least a portion of the proximal end 104 of the implant so that they remain in rotational alignment. In one aspect, the distal end 202 is saddle-shaped, where portions of the implant fit in the seat of the saddle, as illustrated in FIG. 12.

Various shapes and sizes for the implant are contemplated. As shown, the implant has a distal end and a proximal end and opposing sides or walls extending therebetween to support the adjacent vertebrae on opposing upper and lower surfaces relative to the height of the implant. In one aspect, the implant comprises a substantially bullet shaped distal end 102 and a longitudinal axis I.sub.L substantially coaxial with the implant aperture. Bullet shaped can mean that the distal end 102 is an elliptical parabaloid, conical, or the like. Such shapes enable the implant to displace the exiting nerve root in an atraumatic fashion. Where the distal end of the elongate cannulated insertion tool is saddle shaped, the proximal end 104 of the implant 100 can be shaped matingly. Similarly, the proximal end of the implant can comprise a convex cylindrical surface, while the distal end 202 of the elongate cannulated insertion tool 200 can comprise a correspondingly concave cylindrical surface. Other mating surfaces are also contemplated.

As illustrated in FIG. 10, the implant can also have two opposing longitudinal gripping facets 130 each defining a ridged surface 132. The ridged surfaces are meant to assist with the implant's ability to grip the adjacent bone structure. In one aspect, the ridges 132 are angled rearwardly in order to assist in preventing the implant 100 from backing out.

Sometimes, it is beneficial to have the means with which to promote bone growth and/or fusion. In one aspect, the implant further defines an implant cavity 140 in communication with the implant aperture 110 and substantially open to at least one, or both, of the gripping facets 130. In this aspect, bone graft material or bone cement can be introduced into the implant cavity 140. The bone graft material can be, for example, autologous bone, allograft bone, bone substitute, osteoinductive agents, and the like.

The implant itself comprises a biocompatible material, capable of being inserted into the body. In one aspect, the bio-compatible material is selected from the group consisting of PolyEtherEtherKetone, ceramic, allograft bone, and PolyEtherEtherKetone with $BaSO_4$. Other biocompatible materials are also contemplated.

Also presented herein is a percutaneous fusion method to correct disc compression. The method, in one aspect, comprises making a posterolateral incision to access the desired spinal motion segment; determining a target level of the disc space 402 between adjacent vertebral bodies 400 for implantation of an implant; locating a path to the disc space at the target level; inserting a guide wire 440 to maintain a path to the disc space 402; sliding the spinal implant along the guide wire 440 to position it into the disc space at the desired position; removing the guide wire; and fixating at least a portion of the desired spinal motion segment.

This first step comprises making a posterolateral incision to access the desired spinal motion segment. In one aspect, the initial access point can be made through Kambin's Triangle 410. Kambin's Triangle, as those skilled in the art will appreciate, is the site of surgical access for posterolateral endoscopic discectomy. It is defined as a right triangle over the dorsolateral disc. The hypotenuse is the exiting nerve, the base (width) is the superior border of the caudal vertebra, and the height is the traversing nerve root.

The method also comprises determining the target level of the disc space between adjacent vertebral bodies 400. Once the target level is established, the method comprises locating a path to the disc space at the target level. This can be accomplished, for example, using a nerve monitoring probe 420 with a transfer sleeve 430. The nerve monitoring probe can measure the proximity of the exiting nerve root. Once measured, in an exemplified aspect, the probe 420 can then be removed, leaving the transfer sleeve 430 in place. In one aspect, the nerve monitoring probe comprises an EMG Navigation system, comprising a blunt-tipped monopolar probe and an exchange cannula.

The method also comprises inserting a guide wire through the transfer sleeve to maintain a path to the disc space. In one aspect, the guide wire 440 can be a Kirschner wire or k-wire. After insertion of the guide wire, one aspect of the method comprises removing the transfer sleeve and placing a dilator 450 over the guide wire. The dilator 450 can be driven into the disc space 402 to distract the vertebral bodies 400.

In one aspect, the next step comprises positioning an access portal 460 into the disc space. For instance, in one exemplified aspect, the surgeon can slide the access portal 460 over the dilator and use an impact sleeve with a mallet to lodge the portal into the disc space. The dilator and guide wire can then be removed, leaving the access portal in place.

Figure 26:
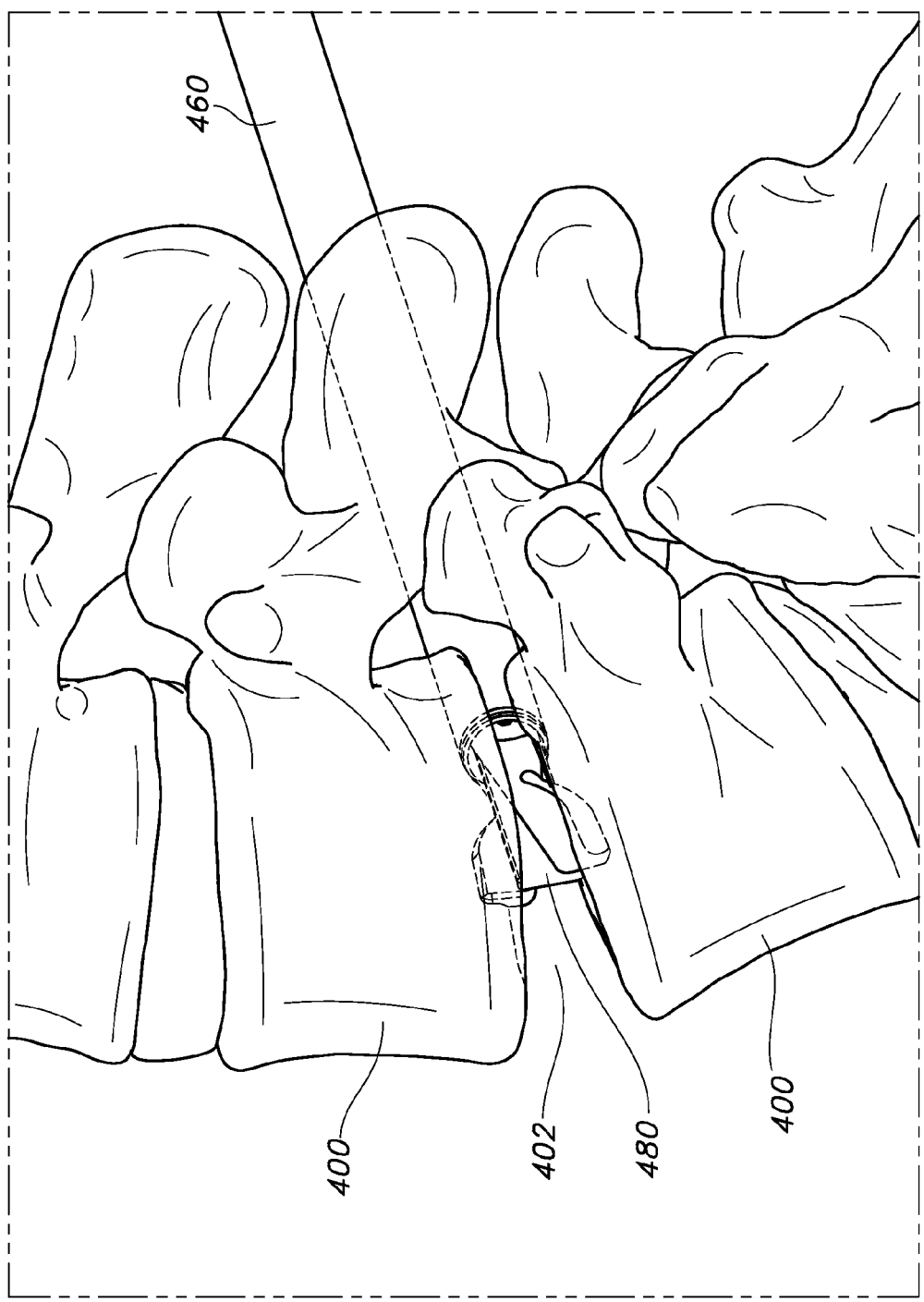
FIG. 26 is a partially transparent perspective view of the method of FIG. 16, showing the step of performing a discectomy and decorticating the vertebral endplates by rotating a disc shaper.
Figure 27:
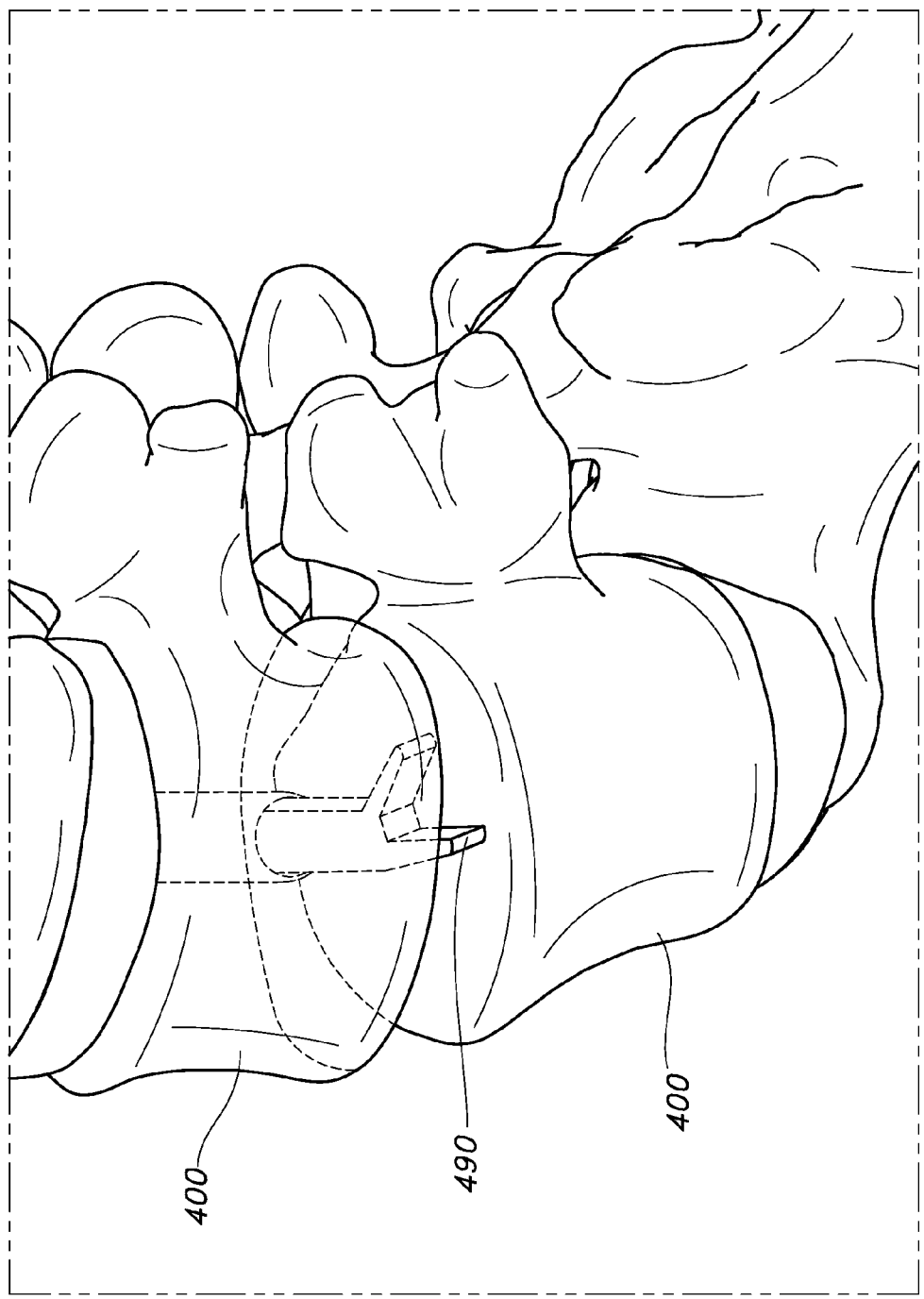
FIG. 27 is a partially transparent perspective view of the method of FIG. 16, showing the step of performing a discectomy and decorticating the vertebral endplates by grasping disc material with a Pituitary rongeur.
Figure 28:
FIG. 28 is a partially transparent perspective view of the method of FIG. 16, showing the step of performing a discectomy and decorticating the vertebral endplates by using a disc cutter.
Figure 29:
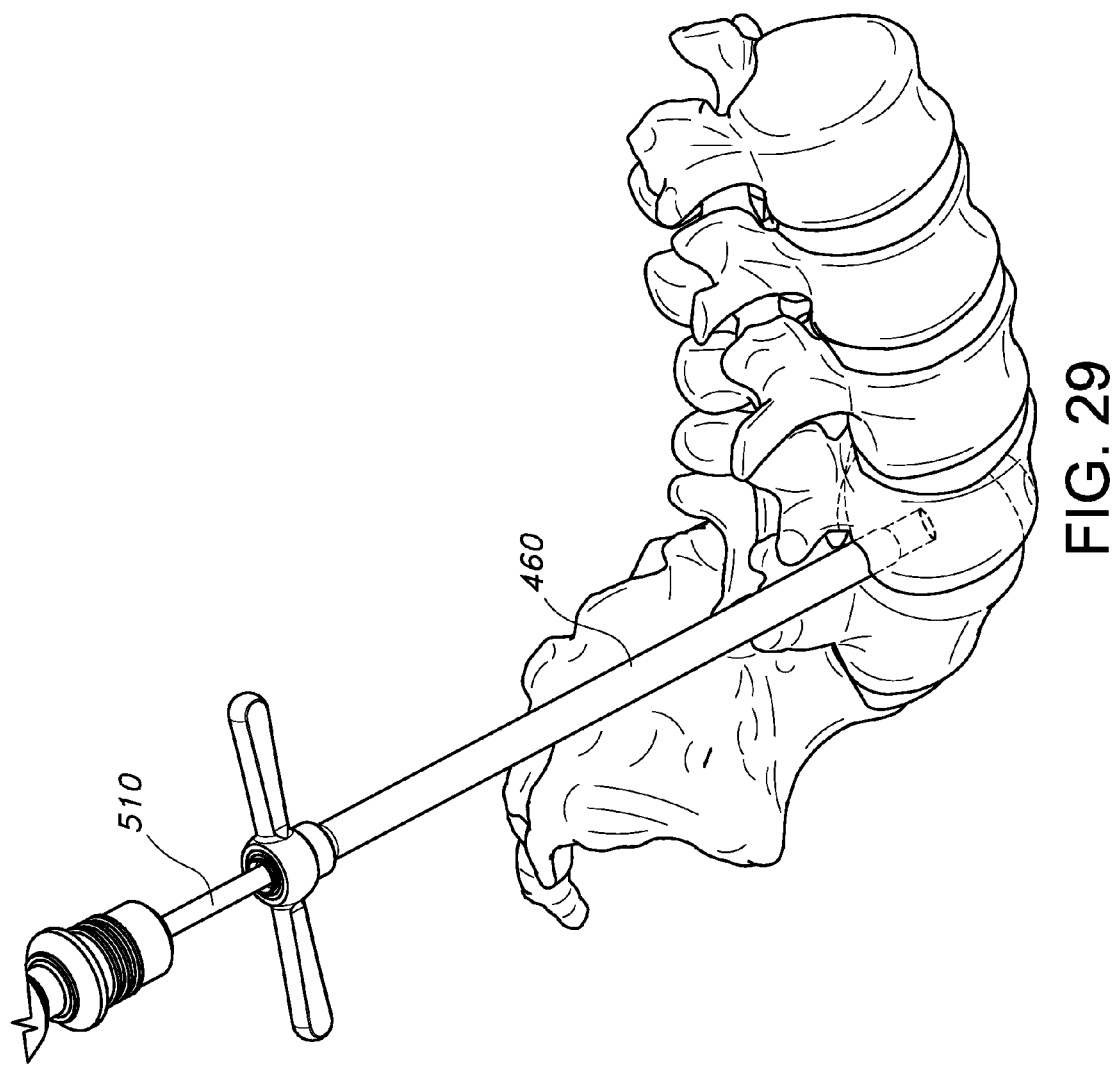
FIG. 29 is a partially transparent perspective view of the method of FIG. 16, showing the step of introducing a bone graft through a portal using a tube and plunger system.
Figure 30:
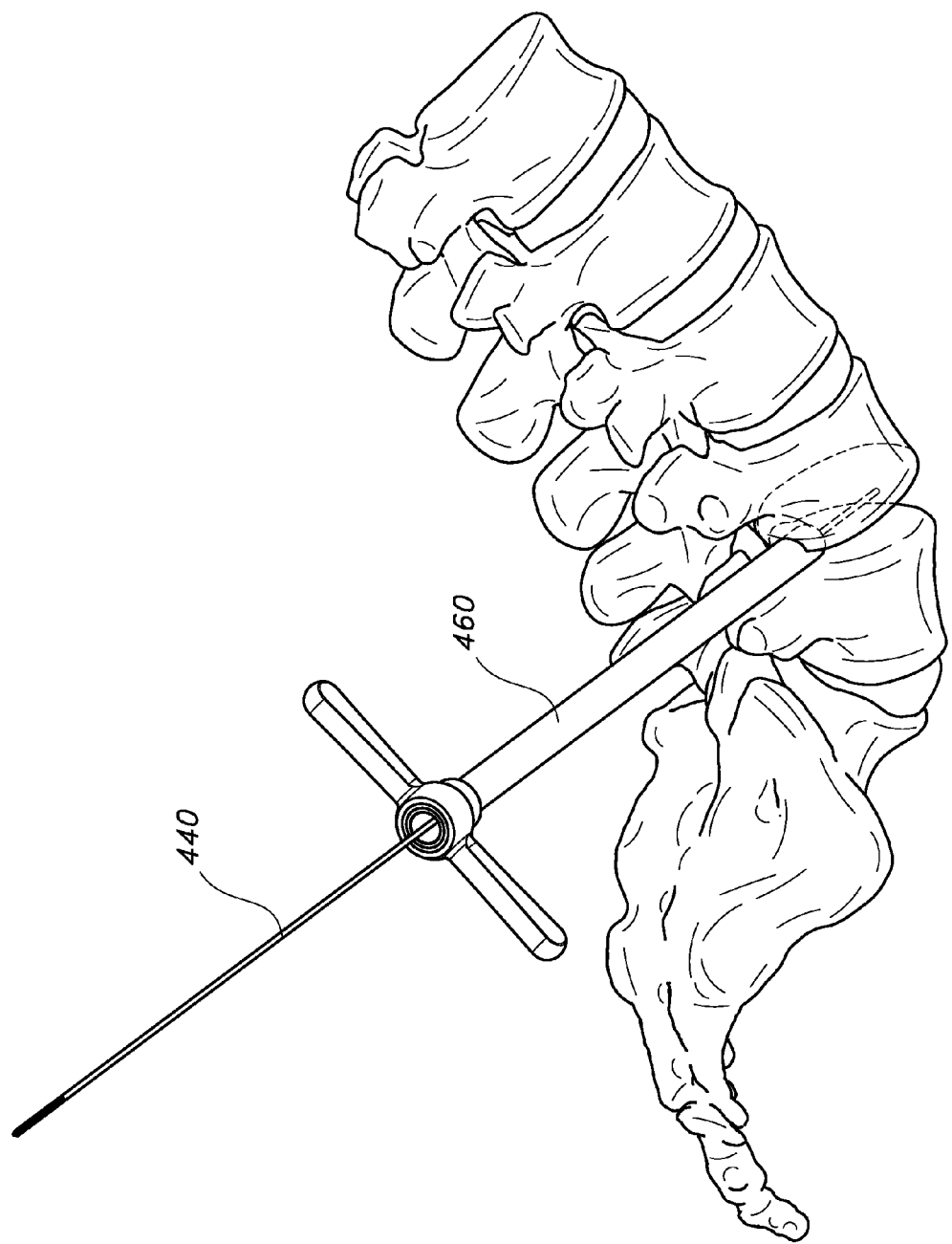
FIG. 30 is a partially transparent perspective view of the method of FIG. 16, showing the step of re-introducing a guide wire through the access portal.
Figure 31:
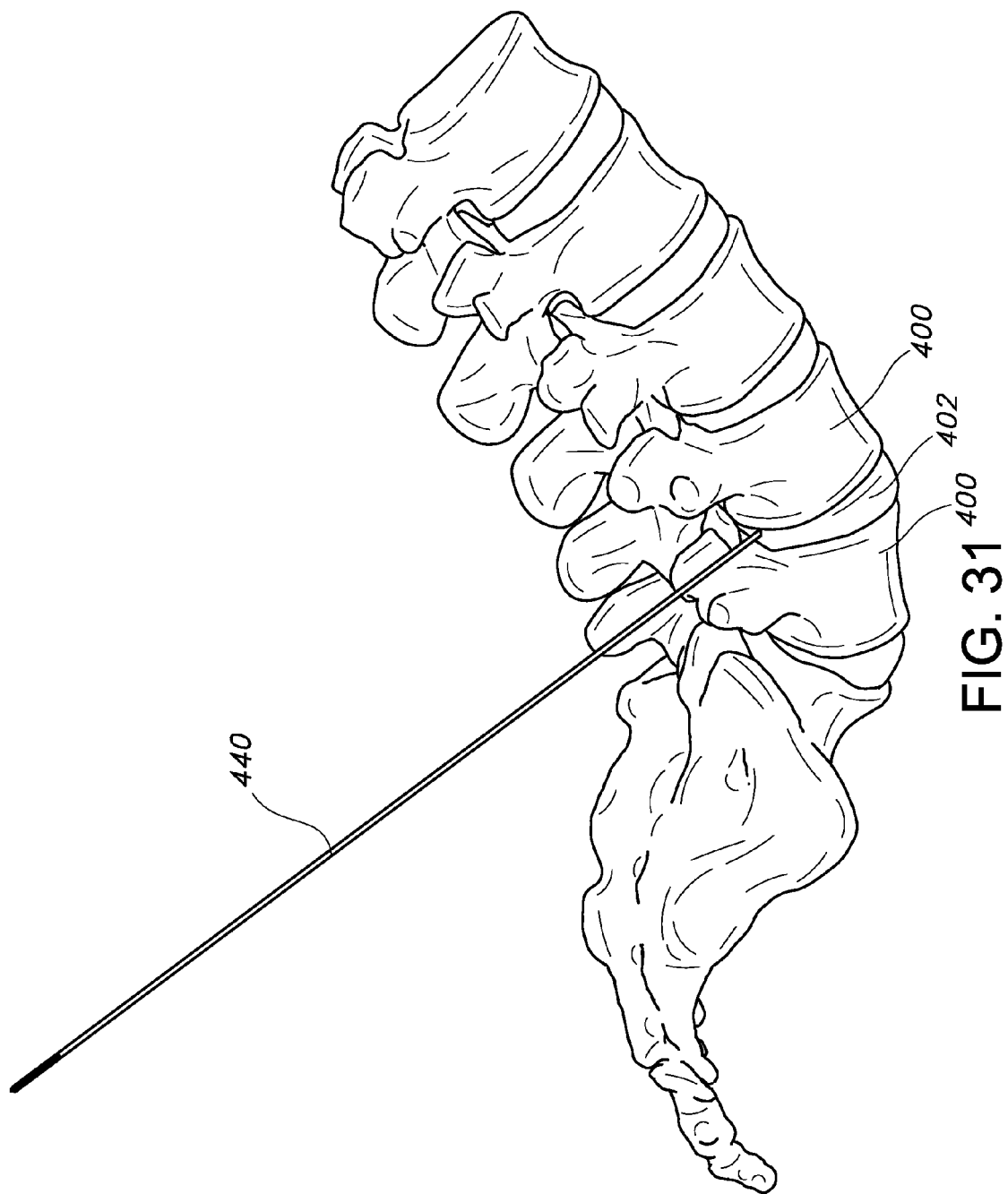
FIG. 31 is a perspective view of the method of FIG. 16, showing the removal of the access portal, leaving the guide wire in place.
Figure 32:
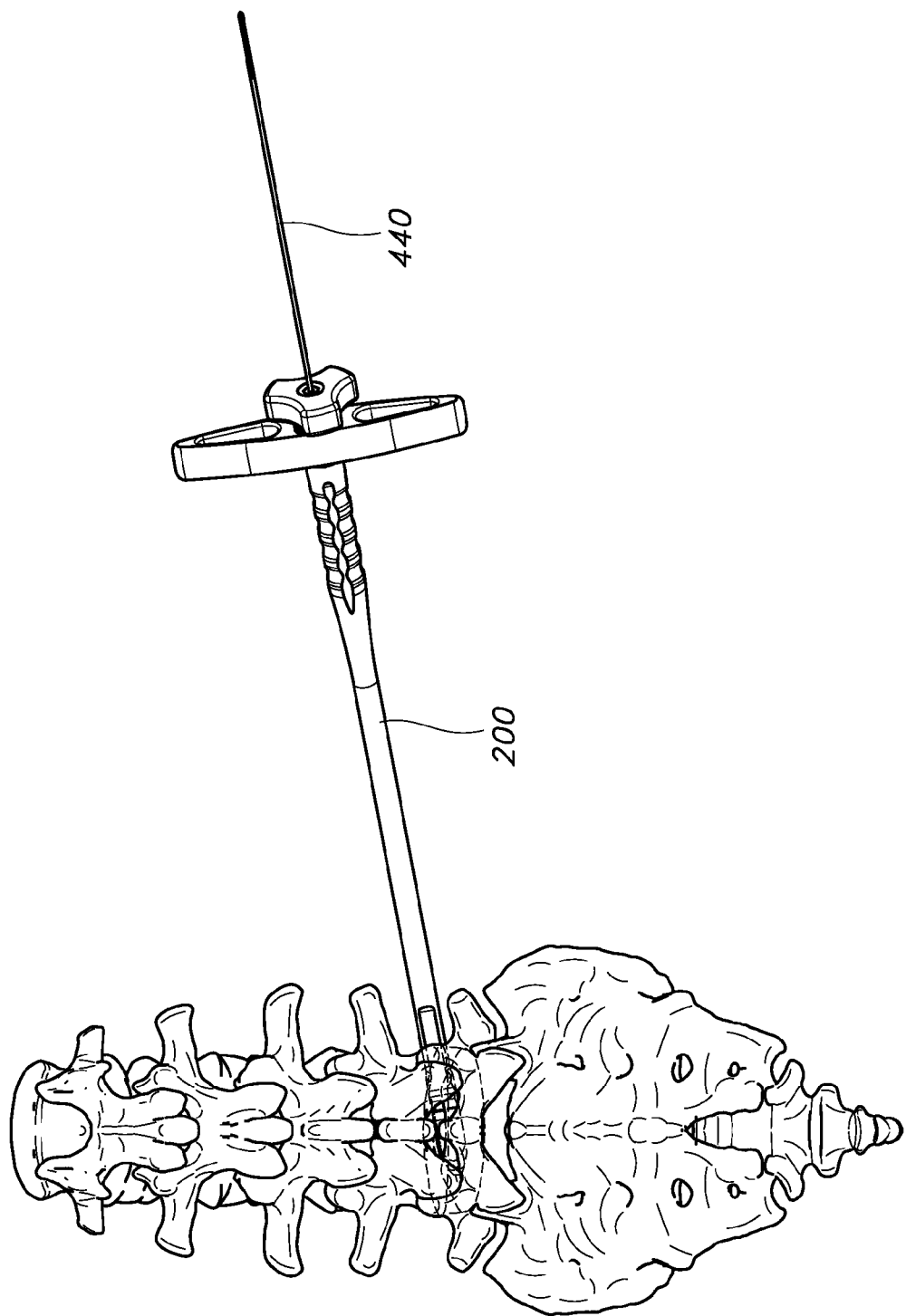
FIG. 32 is a partially transparent perspective view of the method of FIG. 16, showing the step of using the guide wire for insertion of a trial implant.
Figure 33:
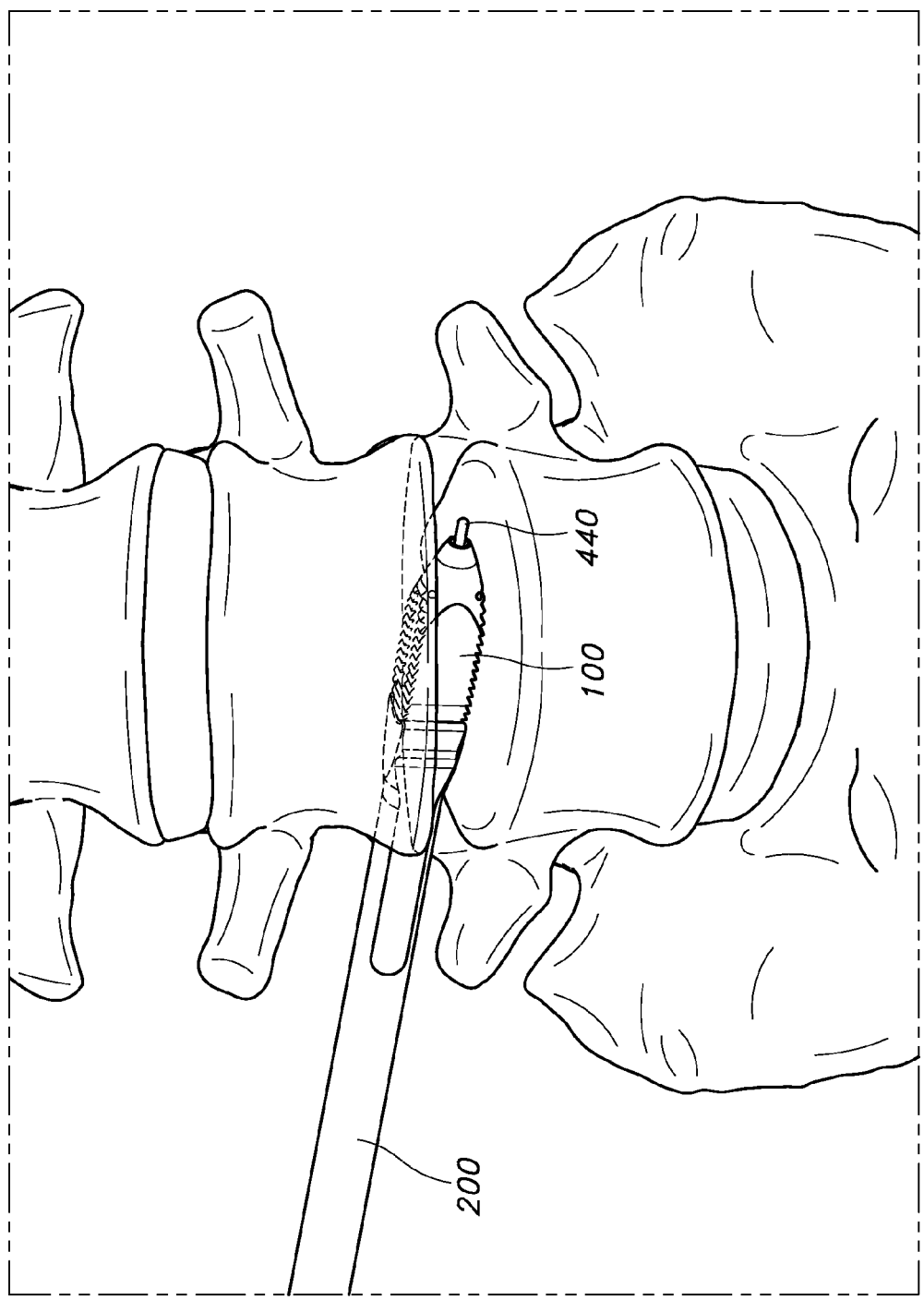
FIG. 33 is a partially transparent perspective view of the method of FIG. 16, showing the step of connecting the implant to the insertion tool and following the guide wire to insert implant.
Figure 34:
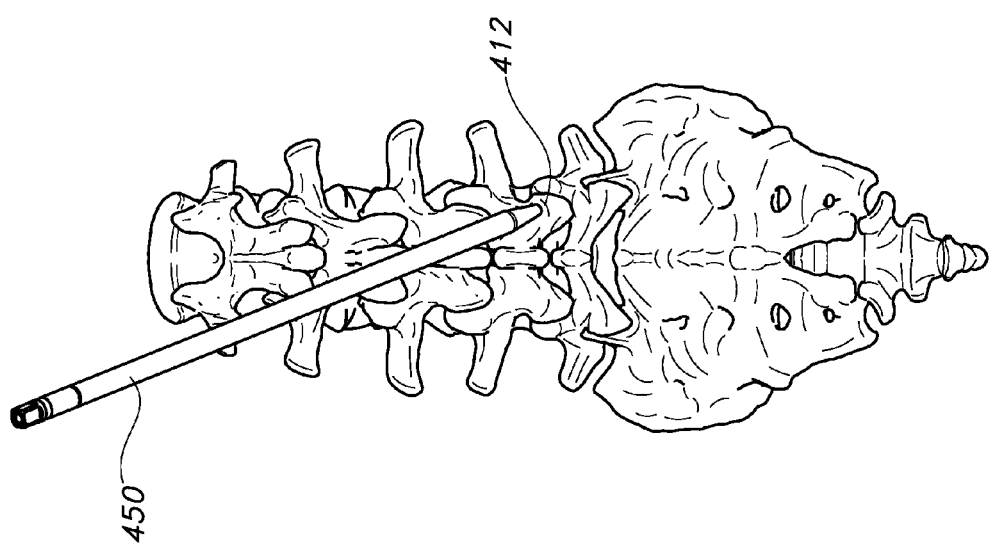
FIG. 34 is a perspective view of the method of FIG. 16, showing the step of using the dilator to locate a path to the appropriate facet joint.
Figure 35:
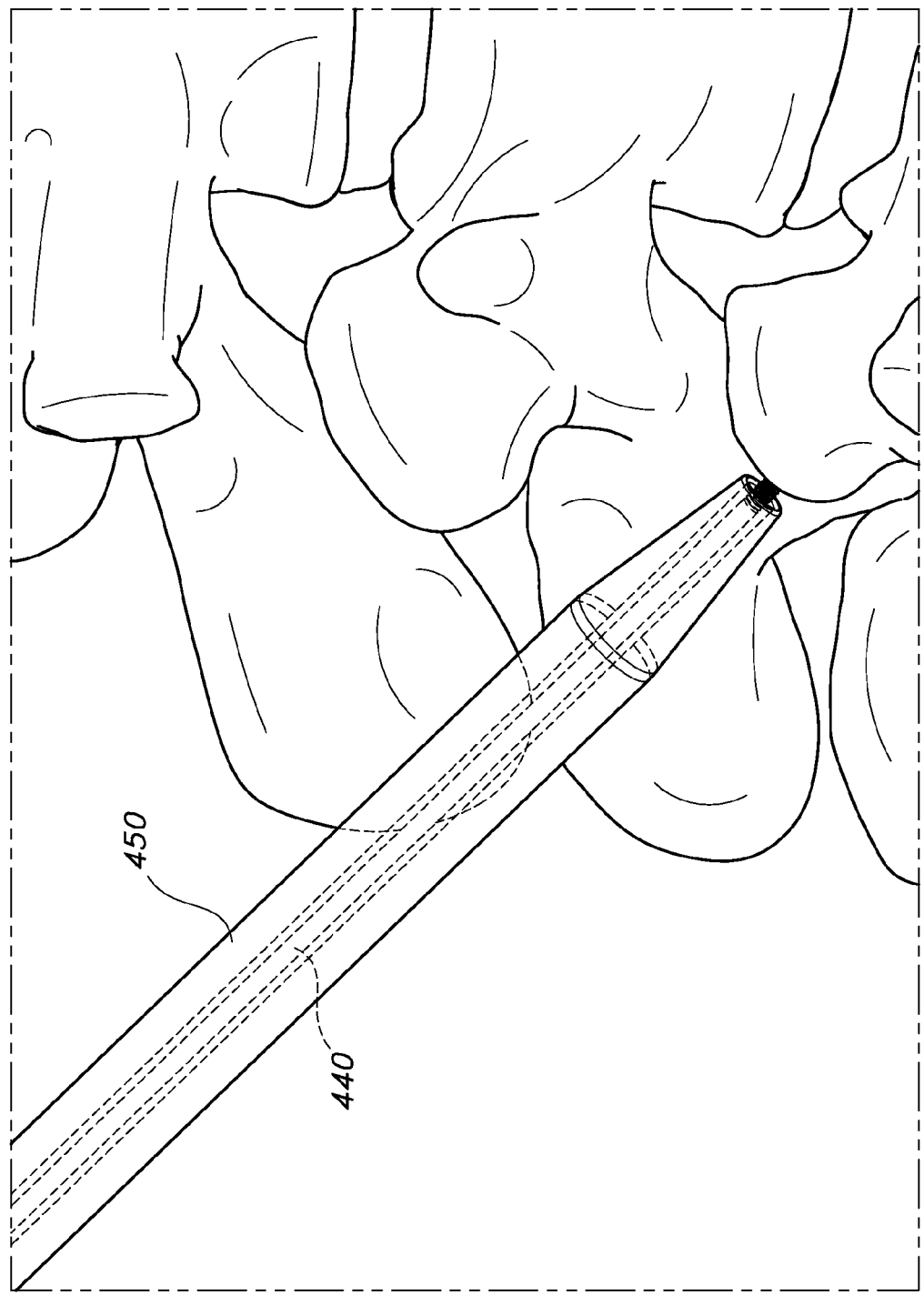
FIG. 35 is a partially transparent perspective view of the method of FIG. 16, showing the step of using a dilator as a guide for introducing the guide wire to a depth just beyond the anticipated depth of the facet screw.
Figure 36:
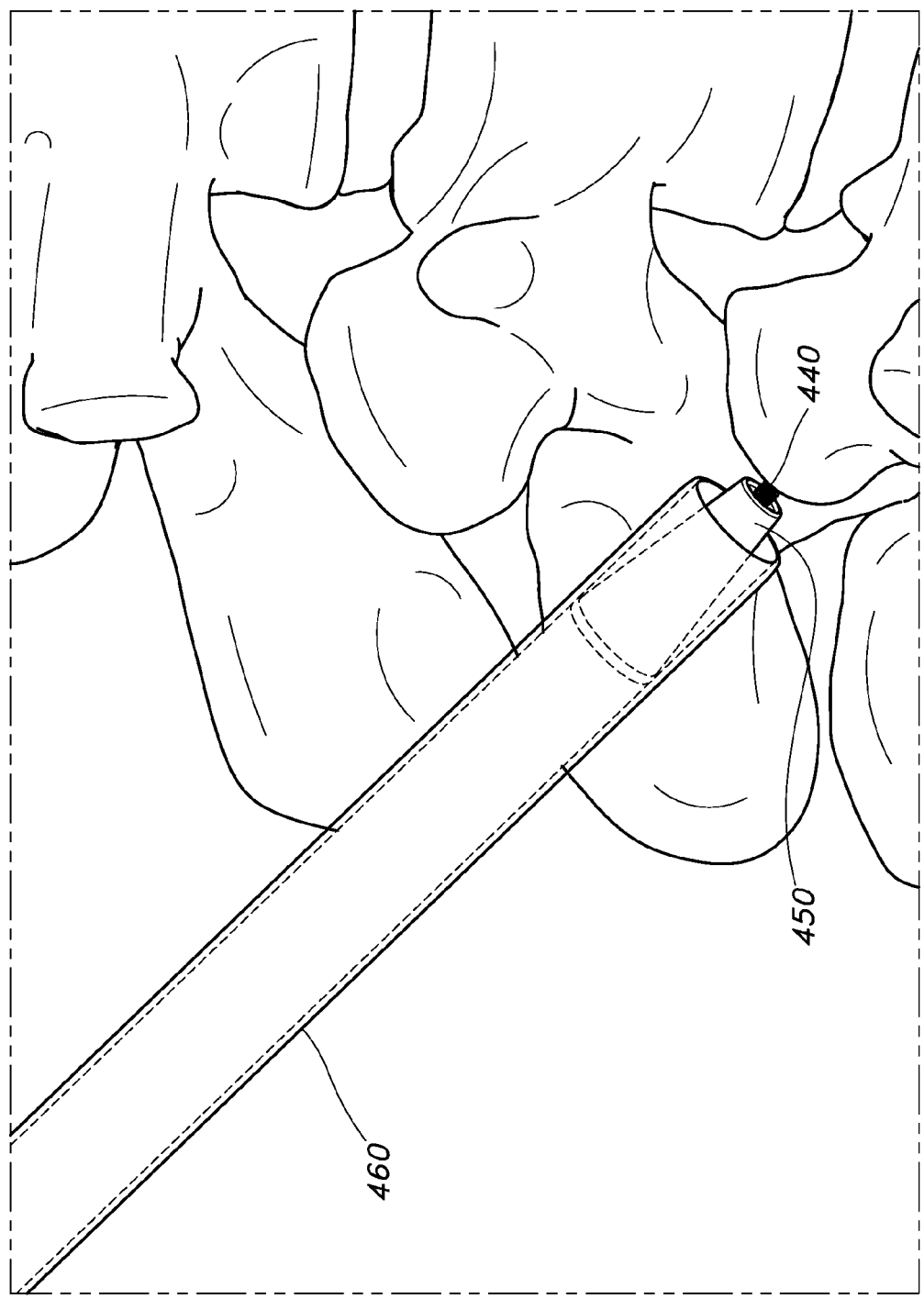
FIG. 36 is a partially transparent perspective view of the method of FIG. 16, showing the step of introducing an access portal over the dilator for facet arthrodesis.
Figure 37:
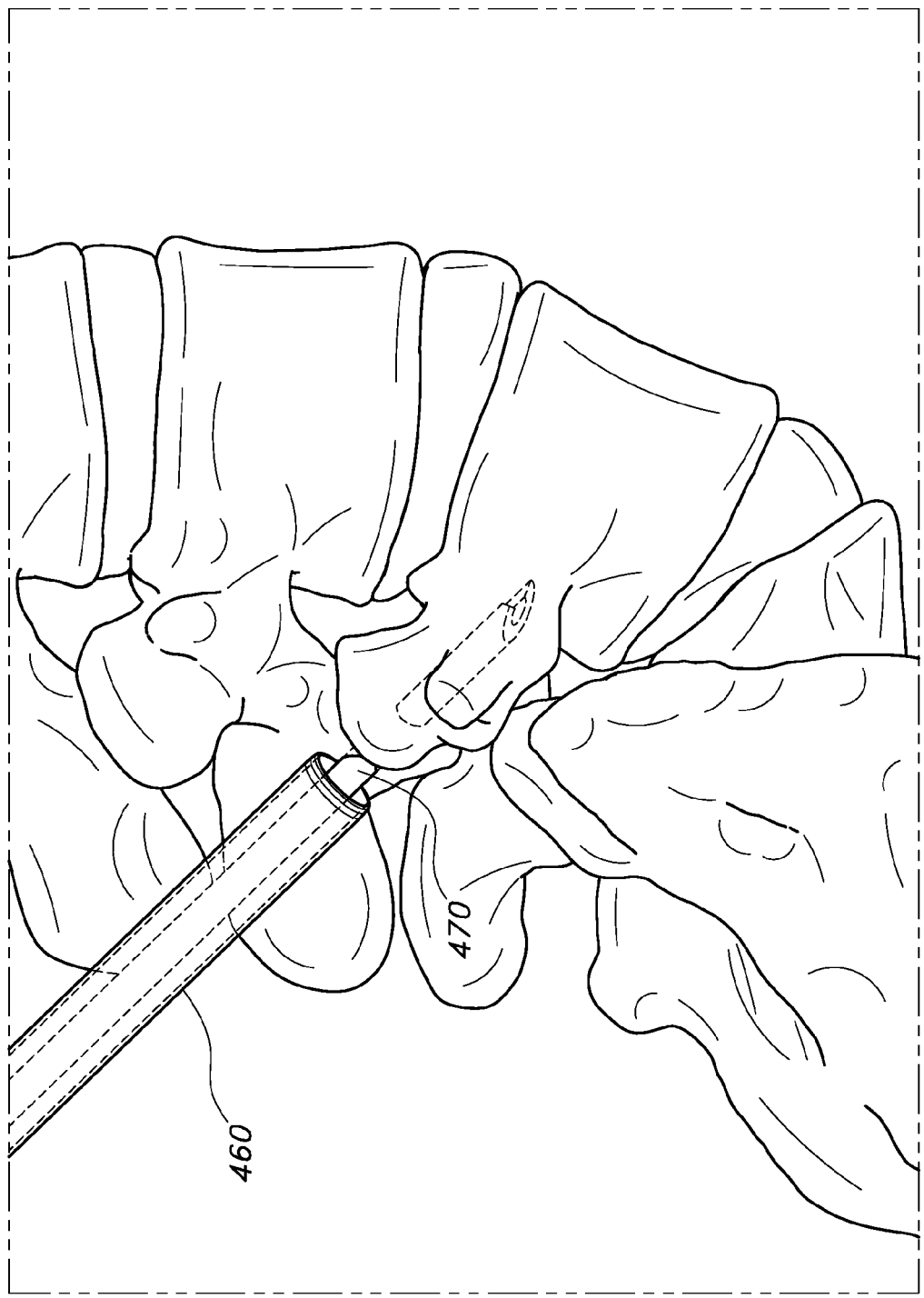
FIG. 37 is a partially transparent perspective view of the method of FIG. 16, showing the step of introducing a drill via the portal to drill through a portion of the facet joint to prepare for insertion of a facet screw.
Figure 38:
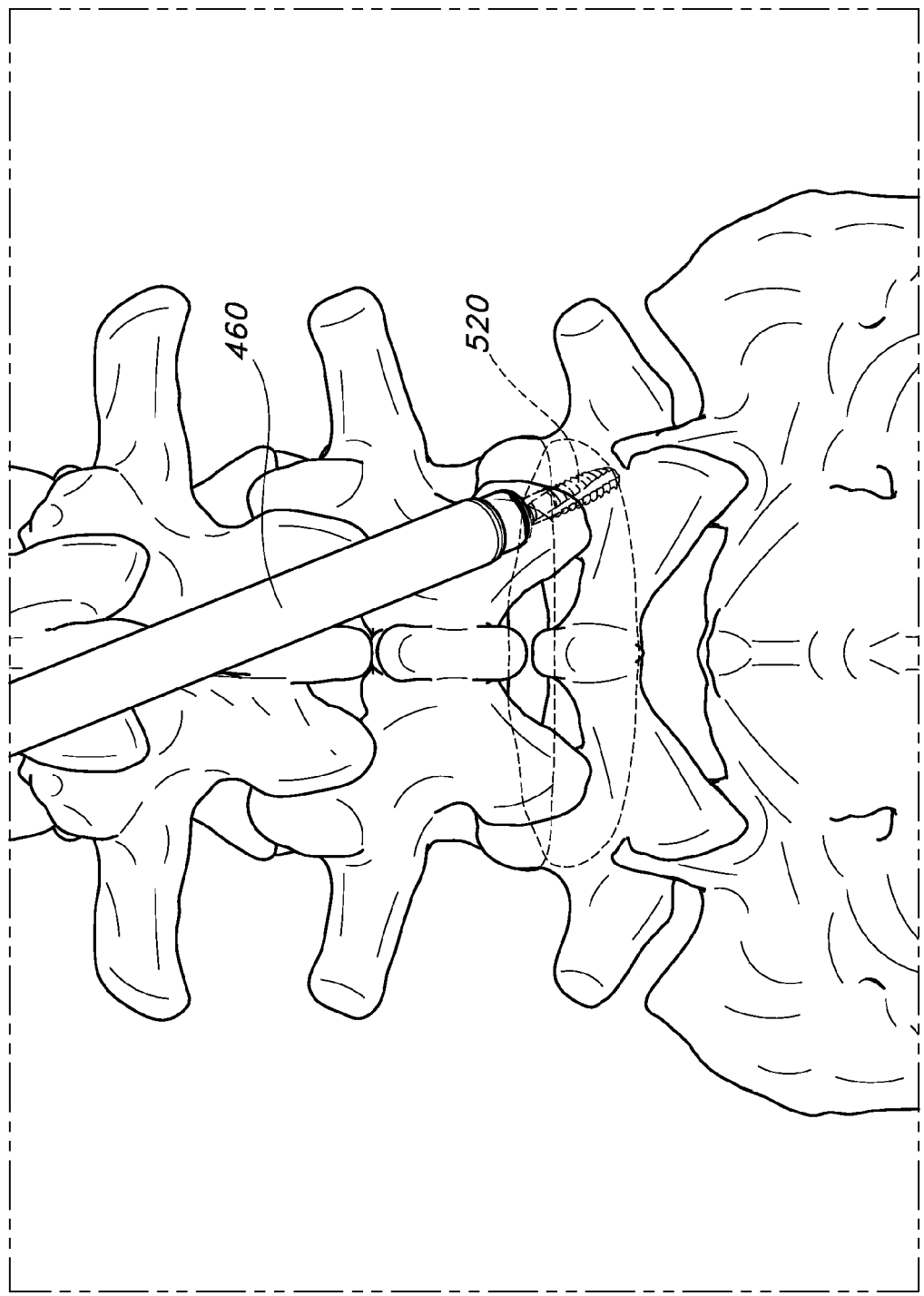
FIG. 38 is a partially transparent perspective view of the method of FIG. 16, showing the step of introduction of the facet screws.
Figure 39:
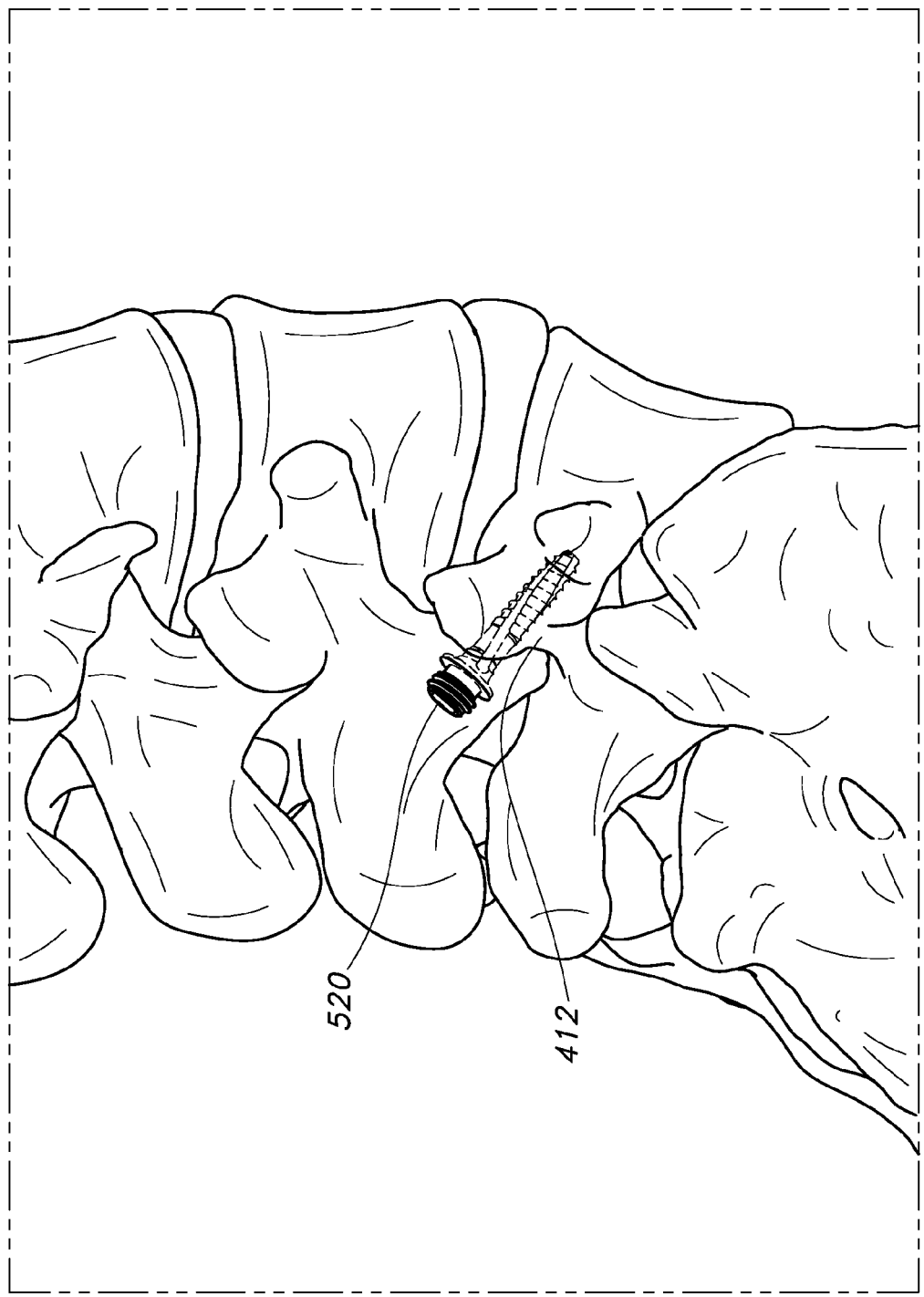
FIG. 39 is a partially transparent perspective view of the method of FIG. 16, showing one aspect of a facet screw in place.

In a further aspect, the method can comprise performing a discectomy and decorticating the vertebral endplates. In an exemplified aspect, a drill 470 can be used to access the nucleus and prepare the area for other discectomy instruments. For example, and not meant to be limiting, a disc shaper 480, as shown in FIG. 26, can be used for endplate preparation. The surgeon may elect to remove some of the loose disc material at this point. As such, a pituitary rongeur 490 can be used. In another aspect, a disc cutter 500, as shown in FIG. 28, can be used to accomplish a thorough discectomy. Afterwhich, the pituitary rongeur 490 can be used again to remove remaining disc remnants.

In one aspect, a bone graft (not shown) can then to be introduced. As one skilled in the art can appreciate, this can be accomplished through the portal using a tube and plunger 510 system. In one aspect, the bone graft is a sentinel bone graft. The surgeon can then re-introduce the guide wire 440 and remove the access portal 460.

With input from pre-surgical radiographic film, the next step can comprise determining the height of an adjacent level healthy disc to assist with the selection of an appropriately sized implant. The size of the implant 100 can be confirmed with a paddle trial or a solid body trial. To do so, the surgeon can first insert the trial implant along a path, guided by the guide wire. An insertion tool 200, as described herein above, may be used. Once inserted, if the selected trial implant cannot be rotated into an erect position, the surgeon can then step down to a smaller size. Alternately, if the selected trail can be rotated into an erect position without much frictional resistance, the surgeon can choose the next larger size. Several iterations may be necessary to achieve the correctly sized implant. As shown in FIGS. 6-10, the implant 100 has an elongated body, the body having a length extending from a distal end to a proximal end. The length is greater than the height or the width of the body of the implant 100. The body has opposing sides or walls extending therebetween the proximal and distal ends to support the adjacent vertebrae on opposing upper and lower surfaces. As shown, from the proximal end 104 view of FIG. 8 or 13 or from a distal end 102 view of FIG. 9 or 14, the substantially square or rectangular cross section midway from the two ends 102, 104 as seen in FIGS. 7 and 10 and also in FIGS. 12 and 15 respectively. The proper height to width ratio is in a range of 1:1 to 2:1 as illustrated. This ratio accommodates the ability to rotate the implant 100 by 90 degrees if desired. The resultant selected height of the implant 100 is based on the height of an adjacent level healthy disc. As noted above, the height of the implant 100 replicates the healthy disc height. The inserted implant, when fully inserted, tenses the soft tissue without damaging the nerves while reestablishing the normal disc height of the vertebral bodies.

As described herein above, in one aspect, the implant 100 comprises an implant cavity 140. As such, the method comprises, after determining the appropriate implant height and length from the trials, loading graft material into the implant cavity and connecting the implant to the insertion tool and following the guide wire to insert the implant. Imaging technology can be used to verify the correct location of the implant. In one aspect, fluorographic imaging can be used to watch radiographic markers in order to determine the correct location of the implant. In one aspect, as determined by the surgeon, when the images show the radiographic markers evenly placed on each side of the spinous processes, the implant is placed properly. Once the implant is placed properly, the surgeon can then turn the implant 90 degrees and release it from the insertion tool 200.

The next step of the method comprises fixating at least a portion of the desired spinal motion segment. In one aspect, this comprises fixating a portion of the facet of the desired disc with a facet screw 520. In one aspect, the facet screw can be a Spartan Facet Screw. For fixation of L5-S1, L4-L5, and/or L3-L4, the surgeon can make an incision substantially proximate the spinous process of L3. Then, the method comprises using the dilator 450 to locate a path to the appropriate inferior articular process. The dilator is used as a guide for introducing the guide wire. In one aspect, the guide wire is delivered by using an electric drill, which delivers the guide wire to a depth just beyond the anticipated depth of the facet screw. Alternate fixation methods include, but are not limited to, pedicle screws, spinous process clamps, and other known fixation methods.

In another aspect, the method also comprises further attaching a neural monitoring lead to the guide wire 440 and stimulating it to a level up to 10 mA to detect the proximity to the exiting nerve roots and cauda equina. Next, the surgeon can place guide wires for all of the facet screws. The dilators could then be removed, leaving the guide wires in place.

The next step in the method comprises performing facet arthrodesis by using a rasp (not shown) capable of removing cartilage, decorticating the joint surfaces. In one aspect, an Amendia Spear disposable rasp may be used. In one aspect, the rasp can comprise a substantially Y-shaped distal end to conform to a portion of the positioned guide wire and move thereabout the guide wire 440. The method comprises using the same incision as with the interbody approach, and inserting a dilator 450 to target the lateral aspect of the facet joint 412. An access portal is, then, introduced over the dilator. Once the portal is positioned, the dilator may be removed. At this point, the appropriate sized rasp can be introduced via the portal 460 to remove cartilage and to decorticate the joint surfaces. After the rasp is removed, the surgeon can, next, load a graft into the delivery tube and insert it into the prepared facet joint 412. In another aspect, this process is repeated through a new incision in a similar location on the contralateral side, targeting the contralateral facet.

In still another aspect, the next step of the method comprises fixating the facet screws. In one aspect, the facet screws may comprise a Spartan Facet Screw. First, the surgeon will re-insert dilators over each of the guide wires. Then, access portals will be introduced via each of the dilators. The dilators can then be removed, leaving the guide wires in place. The surgeon will then deliver the drill bit 470 over the guide wire, penetrating the superior articular process of the inferior vertebral body and drill into the pedicle of the inferior vertebral body.

In one aspect, the facet screws can, then, be introduced, for example, with a screw retaining driver. The method can comprise driving a lag screw to a desired depth to compress the facet joint onto the graft. Alternately, a facet screw with threads along the full length may be used to immobilize the facet joint. At this point, the retaining driver can be released from the implanted screw and the steps of this aspect can be repeated for all levels, bilaterally.

In yet another aspect, the method further comprises performing a foramen nerve root or central decompression, if the surgeon determines that this step is required.

Although several embodiments of the invention have been disclosed in the foregoing specification, it is understood by those skilled in the art that many modifications and other embodiments of the invention will come to mind to which the invention pertains, having the benefit of the teaching presented in the foregoing description and associated drawings. It is thus understood that the invention is not limited to the specific embodiments disclosed herein above, and that many modifications and other embodiments are intended to be included within the scope of the appended claims. Moreover, although specific terms are employed herein, as well as in the claims which follow, they are used only in a generic and descriptive sense, and not for the purposes of limiting the described invention, nor the claims which follow.

We claim:

1. A system for performing spine surgery, comprising: an elongated spinal implant having a substantially square or substantially rectangular cross section midway from a proximal or distal end with a height to width ratio in a range of 1:1 to 2:1 sized for full insertion between two adjacent vertebrae, the implant having a body, the body having a distal end, a proximal end, a length extending from the distal end to the proximal end, opposing sides or walls extending between the distal and proximal ends to support the adjacent vertebrae on opposing upper and lower surfaces, the length being greater than the width or the height of the body of the implant, the body having a longitudinal axis, the body being aligned with the longitudinal axis, the body defining at least one implant aperture, the at least one implant aperture defining openings at the proximal and distal ends of the implant in alignment with one another and the longitudinal axis to allow passage of a straight guide wire therethrough the body, the distal end being an atraumatic tapered distal end, the tapered distal end having a profile having a cross-section along the length of the body of a frustoconical shape or an elliptic parabolic shape; an elongate cannulated insertion tool defining an interior insertion tool pathway, wherein a distal end of the elongate cannulated insertion tool has a concave surface that correspondingly matingly engages at least a portion of a corresponding convex external surface of the implant so rotational alignment of the insertion tool and the implant is maintained to accommodate a 90 degree rotation after insertion if desired to tense the soft tissue without damaging the nerve to reestablish the normal disc height of the two adjacent vertebral bodies; and an elongate lockshaft positioned therein the insertion tool pathway and defining a longitudinal interior lockshaft pathway, wherein a distal end of the elongate lockshaft selectively engages and attaches to a portion of the implant, wherein the proximal opening of the implant has internal threads and at least a portion of the distal end of the elongate lockshaft has external threads that mate with the internal threads of the proximal opening and wherein rotation of the elongate lockshaft can draw and tighten the matingly engaged surfaces of the insertion tool to the implant, wherein when the distal end of the elongate lockshaft is engaged with a proximal end portion of the implant, the interior lockshaft pathway and the implant aperture are aligned to receive the straight guide wire, the implant having a height and a length sized to accommodate being evenly spaced on each side of the spinous process.

2. The system of claim 1, wherein at least a portion of the concave surface is a cylindrical surface.

3. The system of claim 1, further comprising a handle positioned in a proximal portion of the elongate cannulated insertion tool, the handle providing visual means to determine the rotational orientation of the implant.

4. The system of claim 1, wherein the implant comprises two opposing longitudinal gripping facets each defining a ridged surface.

5. The system of claim 4, wherein the implant further defines an implant cavity in communication with the implant aperture and open to at least one of the gripping facets.

6. The system of claim 1, wherein a proximal end of the elongate cannulated insertion tool comprises internal threads and at least a portion of a proximal end of the elongate lockshaft comprises external threads that mate with the internal threads of the cannulated insertion tool such that rotation of the lockshaft in a clockwise direction moves the lockshaft longitudinally within the cannulated insertion tool in a first direction and rotation of the lockshaft in a counterclockwise direction moves the lockshaft longitudinally within the cannulated insertion tool in a second, opposed direction.

7. The system of claim 6, further comprising a knob positioned on a portion of the proximal end of the lockshaft to enable rotation of the lockshaft about a longitudinal axis.

8. A system for performing spine surgery, comprising: an elongated spinal implant defining at least one implant aperture therethrough, the implant having a substantially square or substantially rectangular cross section midway from a proximal or distal end with a height to width ratio in a range of 1:1 to 2:1 sized for full insertion between two adjacent vertebrae, the implant having a body, the body having a distal end, a proximal end, a length extending from the distal end to the proximal end, opposing sides or walls extending between the distal and proximal ends to support the adjacent vertebrae on opposing upper and lower surfaces, the length being greater than the width or the height of the body of the implant, the body having a longitudinal axis, the body being aligned with the longitudinal axis, the at least one implant aperture defining openings at the proximal and distal ends of the implant in alignment with one another and the longitudinal axis to allow passage of a straight guide wire therethrough the body, the distal end being an atraumatic tapered distal end, the tapered distal end having a profile having a cross-section along the length of the body of a frustoconical shape or an elliptic parabolic shape; an elongate cannulated insertion tool defining an interior insertion tool pathway, wherein a distal end of the elongate cannulated insertion tool has a concave surface that correspondingly matingly engages at least a portion of a corresponding convex external surface of the implant to maintain rotational alignment of the insertion tool and the implant to accommodate a 90 degree rotation after insertion if desired to tense the soft tissue without damaging the nerve to reestablish the normal disc height of the two adjacent vertebral bodies; and an elongate lockshaft positioned therein the insertion tool pathway and defining a longitudinal interior lockshaft pathway, wherein a distal end of the elongate lockshaft selectively engages and attaches to a proximal end portion of the implant, wherein the proximal opening of the implant has internal threads and at least a portion of the distal end of the elongate lockshaft has external threads that mate with the internal threads of the proximal opening and wherein rotation of the elongate lockshaft can draw and tighten the matingly engaged surfaces of the insertion tool to the implant, such that, when engaged, the interior lockshaft pathway and the implant aperture are aligned to receive the straight guide wire, the implant having a height and a length sized to accommodate being evenly spaced on each side of the spinous process, wherein a proximal end of the elongate cannulated insertion tool comprises internal threads and at least a portion of a proximal end of the elongate lockshaft comprises external threads that mate with the internal threads of the cannulated insertion tool such that rotation of the lockshaft in a clockwise direction moves the lockshaft longitudinally within the cannulated insertion tool in a first direction and rotation of the lockshaft in a counterclockwise direction moves the lockshaft longitudinally within the cannulated insertion tool in a second, opposed direction.

9. The system of claim 8, wherein at least a portion of the concave surface is a cylindrical surface.

10. The system of claim 8, further comprising a handle positioned in a proximal portion of the elongate cannulated insertion tool, the handle providing visual means to determine the rotational orientation of the implant.

11. The system of claim 8, wherein the implant comprises two opposing longitudinal gripping facets each defining a ridged surface.

12. The system of claim 11, wherein the implant further defines an implant cavity in communication with the implant aperture and open to at least one of the gripping facets.

13. The system of claim 8, further comprising a knob positioned on a portion of the proximal end of the lockshaft to enable rotation of the lockshaft about a longitudinal axis.

* * * * *